(12) United States Patent
Higashi

(10) Patent No.: US 8,404,652 B2
(45) Date of Patent: Mar. 26, 2013

(54) DNA-BINDING PROTEIN YB-1-CONTAINING COLLAGEN ACCUMULATION INHIBITORS

(75) Inventor: Kiyoshi Higashi, Osaka (JP)

(73) Assignee: Sumitomo Chemical Company, Limited, Osaka (JP)

( * ) Notice: Subject to any disclaimer, the term of this patent is extended or adjusted under 35 U.S.C. 154(b) by 0 days.

(21) Appl. No.: 09/972,331

(22) Filed: Oct. 9, 2001

(65) Prior Publication Data

US 2002/0091083 A1    Jul. 11, 2002

(30) Foreign Application Priority Data

Oct. 11, 2000    (JP) .................................. 2000-310624

(51) Int. Cl.
*A61K 48/00*    (2006.01)
*C07H 21/04*    (2006.01)
(52) U.S. Cl. ..................................... 514/44 R; 526/23.1
(58) Field of Classification Search ..................... 514/44
See application file for complete search history.

(56) References Cited

U.S. PATENT DOCUMENTS 6,140,126 A    10/2000    Bennett et al.

FOREIGN PATENT DOCUMENTS

WO    WO 01/02556 A2    1/2001

OTHER PUBLICATIONS

Verma et al., Nature, 389:239-242 (1997).*
Palu et al. J. Biotechnol., 68:1-13 (1999).*
Fox, ASM News, 66 (2): 1-13, Feb. 2000.*
Nakao et al., J. Clin. Investi., 104 (1), 5-11, Jul. 1999.*
Kashanchi et al., J. Virology, Jan. 1994, vol. 68, No. 1, p. 561-565.*
Sun et al., Matrix Biology 20 (2001) 527-541.*
Chen et al.a, J. Virol., vol. 69, No. 9, Sep. 1995, p. 5843-5848.*
Norman et al., "The Y-Box Binding Protein YB-1 Suppresses Collagen α1 (I)Gene Transcription Via An Evolutionarily Conserved Regulatory Element in the Proximal Promoter," J. Biol. Chem., 10.1074/jbc.M103145200, Jun. 5, 2001.
Baroni et al., "Interferon Gamma Decreases Hepatic Stellate Cell Activation and Extracellular Matrix Deposition in Rat Liver Fibrosis", Hepatology, pp. 1189-1198, (May 1996).
Broekelmann et al., "Transforming Growth Factor β1 is Present At Sites of Extracellular Matrix Gene Expression in Human Pulmonary Fibrosis", Proc. Natl. Acad. Sci, USA, vol. 88, pp. 6642-6646, (Aug. 1991).
Dhalla et al., "chk-YB-1b, a Y-box Binding Protein Activates Transcription From Rat α1(1) Procollagen Gen Promoter", Biochem. J. (1998), pp. 373-379.
Ghosh et al., "Antagonistic Regulation of Type I Collagen Gene Expression by Interferon-γ and Transforming Growth Factor-β", the Journal of Biol. Chem., Volm 276, No. 14, pp. 11041-11048 (Apr. 6 Issue).
Higashi et al., A Proximal Element Within the Human α2(I) Collagen (COL1A2) Promoter, Distinct From the Tumor Necrosis Factor-α Response Element, Mediates Transcriptional Repression by Interferon-γ, Matrix Biology, vol. 16/1997/98, pp. 447-456.
Jaffe & Gao, "Selective Inhibition of Collagen Gene Expression in Fibroblasts by an Interferon-γ Transgene", Experimental Lung Research, 25: pp. 199-215 (1999).
Norman et al., "The Y-Box Binding Protein YB-1 Suppresses Collagen α1(I) Gene Transcription Via An Evolutionarily Conserved Regulatory Element in the Proximal Promoter", The J. of Biol. Chem., vol. 276, No. 32, pp. 29890-29890, (Aug. 10 Issue).

* cited by examiner

*Primary Examiner* — Nancy T Vogel
(74) *Attorney, Agent, or Firm* — Fitch, Even, Tabin & Flannery, LLP

(57) ABSTRACT

The present invention provides a collagen accumulation inhibitor, a collagen accumulation-inhibiting method, a method for searching for a substance which regulates the type-I collagen gene transcription regulating ability and the like, said matters being useful in a medical field for a prophylaxis or the treatment of a disease caused by an excessive accumulation for a collagen (for example fibrosis).

14 Claims, No Drawings

DNA-BINDING PROTEIN YB-1-CONTAINING COLLAGEN ACCUMULATION INHIBITORS

BACKGROUND OF THE PRESENT INVENTION

1. Field of the Present Invention

The present invention relates to a DNA-binding protein YB-1-containing collagen accumulation inhibitor.

2. Description of the Related Art

In cases of diseases and abnormalities such as liver cirrhosis, interstitial pulmonary disease, chronic renal insufficiency (or a disease leading to a chronic renal insufficiency), postinflammatory hyperplastic scar, postoperative scar or burn scar, or scleroderma, arteriosclerosis, hypertension, rheumatoid arthritis and the like, an excessive integration of a extracellular matrix such as a collagen leads to a fibrotic and hard tissue, resulting in a dysfunction of an organ or tissue as well as a scar formation. Such excessive integration of an extracellular matrix is induced by an impaired balance between the biosynthesis and the degradation of a collagen which leads to an excessive production. In fact, it was observed that a tissue once in a fibrotic state underwent an increased expression of a collagen gene, especially of a type-I collagen gene [J. Invest. Dermatol., 94, 365, (1990), Proc. Natl. Acad. Sci. USA, 88, 6642 (1991)]. Also in various animal models of fibroses, a treatment with interferon gamma reduces the expression of a type-I collagen gene in a tissue, resulting in a reduced amount of the collagen, which leads to a recovery from a fibrotic state of the tissue [Exp. Lung Res., 21, 791-808, (1995), Kidney Int., 47, 62-69, (1995), J. Hepatol., 28, 471-479 (1998), J. Hepatol., 26, 894-903 (1997)]. It was also reported that the level of TGFβ, which is one of cytokines, was increased in a tissue once in a fibrotic state [J. Invest. Dermatol., 94, 365 (1990), Proc. Natl. Acad. Sci. USA, 88, 6642 (1991)]. TGFβ was also reported to increase the expression of a type-I collagen gene and to be involved in an excessive production of the collagen, thus also in the conversion of a tissue into a fibrotic state [Lab. Invest., 63, 171, (1990), J. Invest. Dermatol., 94, 365 (1990)].

SUMMARY OF THE PRESENT INVENTION

Accordingly, there is a demand for the development of a method or a pharmaceutical which inhibits an excessive expression of a type-I collagen gene in a tissue whereby suppressing an excessive production of the collagen and thus being useful in the prophylaxis or the treatment of a disease or an abnormality accompanying an excessive integration of an extracellular matrix.

The present inventors made an effort under the circumstance described above and finally discovered that a DNA-binding protein having a certain amino acid sequence inhibits the transcription of a type-I collagen gene, whereby inhibiting the accumulation of the collagen. Based on these findings, we established a collagen accumulation inhibitor, a collagen accumulation-inhibiting method, a method for searching for a substance which regulates the type-I collagen gene transcription regulating ability and the like, said matters being useful in a medical field for a prophylaxis or the treatment of a disease caused by an excessive accumulation for a collagen (for example fibrosis). thus reaching the present invention.

Accordingly, this invention provides:

1. A collagen accumulation inhibitor containing as an active ingredient a DNA-binding protein having any of the following amino acid sequences:

<Amino Acid Sequences>
   (a) the amino acid sequence represented by SEQ ID No:.1;
   (b) an amino acid sequence which is formed as a result of the deletion, addition or substitution of at least one amino acid in the amino acid sequence represented by SEQ ID No:.1 and which is an amino acid sequence of a protein having an ability of inhibiting the transcription of a type-I collagen gene;
   (c) an amino acid sequence whose sequence identity with the amino acid sequence represented by SEQ ID No:.1 is 80% or more and which is an amino acid sequence of a protein having an ability of inhibiting the transcription of a type-I collagen gene;
   (d) an amino acid sequence encoded by a DNA having a nucleotide sequence whose sequence identity with a DNA having a nucleotide sequence encoding the amino acid sequence represented by SEQ ID No:.1 is 90% or more and which is an amino acid sequence of a protein having an ability of inhibiting the transcription of a type-I collagen gene; and,
   (e) an amino acid sequence encoded by a DNA capable of being hybridized under a stringent condition with a DNA having a nucleotide sequence encoding the amino acid sequence represented by SEQ ID No:.1 and which is an amino acid sequence of a protein having an ability of inhibiting the transcription of a type-I collagen gene; wherein said active ingredient is formulated with a pharmaceutically acceptable carrier;

(Hereinafter, the above-mentioned amino acid sequences are sometimes referred to as the amino acid sequences (I).)

2. A collagen accumulation inhibitor containing as an active ingredient a polynucleotide encoding a DNA-binding protein having any of the amino acid sequences (I), wherein said active ingredient is formulated with a pharmaceutically acceptable carrier;

3. A use of a DNA-binding protein having any of the amino acid sequences (I) for inhibiting a collagen accumulation;

4. A use of a polynucleotide encoding a DNA-binding protein having any of the amino acid sequences (I) for inhibiting a collagen accumulation;

5. A use of a DNA-binding protein having any of the amino acid sequences (I) for inhibiting the transcription of a type-I collagen gene;

6. A use of a polynucleotide encoding a DNA-binding protein having any of the amino acid sequences (I) for inhibiting the transcription of a type-I collagen gene;

7. A method for inhibiting a collagen accumulation in mammals comprising a step for providing an exogenous gene encoding a DNA-binding protein having any of the amino acid sequences (I) to a mammalian cell so that said exogenous gene is located in a position enabling its expression in said cell;

8. The method for inhibiting a collagen accumulation according to the above 7 wherein said exogenous gene is provided to a mammalian cell under a condition allowing a positive regulatory factor of a collagen accumulation-promoting pathway to be present outside of said cell.

9. The method for inhibiting a collagen accumulation according to the above 8 wherein the positive regulatory factor of a collagen accumulation-promoting pathway is a positive regulatory factor of a DNA-binding protein-dependent collagen accumulation promoting pathway.

10. The method for inhibiting a collagen accumulation according to the above 9 wherein the DNA-binding protein is an AP-1 or a Smad.

11. The method for inhibiting a collagen accumulation according to the above 8 wherein the positive regulatory factor of a collagen accumulation-promoting pathway is a TGF-β.

12. A method for inhibiting a collagen accumulation comprising a step for administering a DNA-binding protein having any of the amino acid sequences (I) to a cell present in a body of a mammal which may be diagnosed to have a disease caused by an excessive accumulation of a collagen;

13. A method for inhibiting a collagen accumulation comprising a step for administering a DNA-binding protein having any of the amino acid sequences (I) to a cell present in a body of a mammal which may be diagnosed to have a fibrosis;

14. A method for inhibiting a collagen accumulation comprising a step for administering a DNA-binding protein having any of the amino acid sequences (I) to a mammalian cell under a condition allowing a positive regulatory factor of a collagen accumulation-promoting pathway to be present outside of said cell;

15. A method for inhibiting a collagen accumulation according to the above 14 wherein the positive regulatory factor of a collagen accumulation-promoting pathway is a positive regulatory factor of a DNA-binding protein-dependent collagen accumulation promoting pathway;

16. A method for inhibiting a collagen accumulation comprising a step for administering a DNA-binding protein having any of the amino acid sequences (I) to a cell having a type-I collagen gene;

17. A method for inhibiting a collagen accumulation comprising a step for administering a DNA-binding protein having any of the amino acid sequences (I) to a cell having a type-I collagen gene under a condition allowing a positive regulatory factor of a collagen accumulation-promoting pathway to be present outside of said cell;

18. The method for inhibiting a collagen accumulation according to the above 17 wherein a positive regulatory factor of a collagen accumulation-promoting pathway is a positive regulatory factor of a DNA-binding protein-dependent collagen accumulation promoting pathway;

19. A method for searching for a substance which regulates the type-I collagen gene transcription regulating ability comprising:
(1) a first step for bringing a test substance into contact with a cell expressing a DNA-binding protein having any of the amino acid sequences (I);
(2) a second step, following to said first step, for measuring the quantity of said DNA-binding protein migrated into the nucleus of a cell or a parameter having a correlation with said quantity;
(3) a third step for evaluating the type-I collagen gene transcription regulating ability of said substance based on the quantity of the migrated protein or the parameter correlating with such quantity, which were determined in the second step; and,
(4) a fourth step for selecting a substance having the type-I collagen gene transcription regulating ability based on the type-I collagen gene transcription regulating ability evaluated in said third step;

20. The method according to the above 19 wherein said cell is a cell expressing an exogenous marker protein capable of providing a parameter having a correlation with the quantity of said DNA-binding protein migrated into the nucleus of the cell;

21. A method for searching for a substance which regulates the type-I collagen gene transcription regulating ability comprising:
(1) a first step for bringing two or more different test substances into contact independently with a cell which has a type-I collagen gene and in which an exogenous gene encoding a DNA-binding protein having any of the following amino acid sequence is provided so that said exogenous gene is located in a position enabling its expression in said cell;
(2) a second step, following to said first step, for monitoring the collagen accumulation quantity independently;
(3) a third step for evaluating the type-I collagen gene transcription regulating ability of said substance based on the difference observed by comparing the collagen accumulation quantities, which were monitored independently in the second step, with each other; and,
(4) a fourth step for selecting a substance having the type-I collagen gene transcription regulating ability based on the type-I collagen gene transcription regulating ability evaluated in said third step;

22. The method according to the above 21 wherein the first step is conducted under a condition allowing a positive regulatory factor of a collagen accumulation-promoting pathway to be present outside of said cell;

23. The method according to the above 22 wherein a positive regulatory factor of a collagen accumulation-promoting pathway is a positive regulatory factor of a DNA-binding protein-dependent collagen accumulation promoting pathway;

24. A method for searching for a substance which regulates the type-I collagen gene transcription regulating ability comprising:
(1) a first step for bringing a test substance into contact independently with each of (a) a cell containing a reporter gene which contains a nucleotide sequence required for initiating a transcription and which is ligated in a functional form to a type-I collagen gene expression regulatory region and (b) a cell containing a reporter gene which contains a nucleotide sequence required for initiating a transcription and which is ligated in a functional form to a nucleotide sequence having no ability of binding to a DNA-binding protein having any of the amino acid sequences (I);
(2) a second step, following to said first step, for monitoring the reporter gene expression quantity independently;
(3) a third step for evaluating the type-I collagen gene transcription regulating ability of said substance based on the difference observed by comparing the expression quantities, which were monitored independently in the second step, with each other; and,
(4) a fourth step for selecting a substance having the type-I collagen gene transcription regulating ability based on the type-I collagen gene transcription regulating ability evaluated in said third step;

25. The method according to the above 24 wherein the first step is conducted under a condition allowing a positive regulatory factor of a collagen accumulation-promoting pathway to be present outside of said cell.

26. The method according to the above 25 wherein a positive regulatory factor of a collagen accumulation-promoting pathway is a positive regulatory factor of a DNA-binding protein-dependent collagen accumulation promoting pathway;

27. A collagen accumulation inhibitor containing as an active ingredient a substance selected by the searching method according to any of the above 19 to 26 or a pharmaceutically acceptable salt thereof wherein said active ingredient is formulated with a pharmaceutically acceptable carrier;

28. A compound represented by general formula (I):

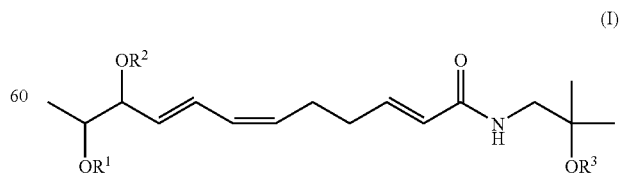

wherein $R^1$, $R^2$ and $R^3$ are same or different and each denotes a hydrogen atom, an alkyl group or an acyl group or a pharmaceutically acceptable salt thereof;

29. A collagen accumulation inhibitor containing as an active ingredient a compound represented by general formula (I):

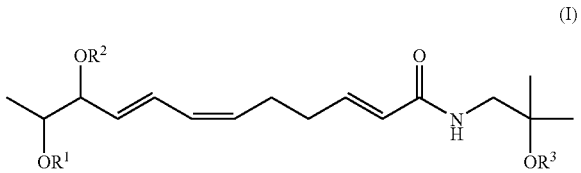

wherein $R^1$, $R^2$ and $R^3$ are same or different and each denotes a hydrogen atom, an alkyl group or an acyl group or a pharmaceutically acceptable salt thereof, wherein said active ingredient is formulated with a pharmaceutically acceptable carrier;

30. A collagen accumulation inhibitor containing as an active ingredient at least one of the parts of a plant selected from the group consisting of angelica (Zanthoxylum piperitum De Candolle) and the same genus plants thereof and linden (Tilia cordata Mill) and the same genus plants thereof or a processed material obtained therefrom wherein said active ingredient is formulated with a pharmaceutically acceptable carrier;

31. A method for inhibiting a collagen accumulation comprising a step for administering a positive regulatory factor of a collagen accumulation-inhibiting pathway which is dependent on a DNA-binding protein having any of the amino acid sequences (I) to a cell having a type-I collagen gene under a condition allowing a positive regulatory factor of a collagen accumulation-promoting pathway to be present outside of said;

32. The method according to the above 31 wherein the positive regulatory factor of a collagen accumulation-promoting pathway is a positive regulatory factor of a DNA-binding protein-dependent collagen accumulation promoting pathway and the like.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step.

DESCRIPTION OF THE PREFERRED EMBODIMENTS

The present invention is detailed below.

The accumulation inhibitor (I) of the present invention is used for inhibiting a collagen accumulation (especially for inhibiting the transcription of a type-I collagen gene).

A DNA-binding protein used in the accumulation inhibitor (I) of the present invention is a protein having any of the following amino acid sequences:

(a) the amino acid sequence represented by SEQ ID No:.1;
(b) an amino acid sequence which is formed as a result of the deletion, addition or substitution of at least one amino acid in the amino acid sequence represented by SEQ ID No:.1 and which is an amino acid sequence of a protein having an ability of inhibiting the transcription of a type-I collagen gene;
(c) an amino acid sequence whose sequence identity with the amino acid sequence represented by SEQ ID No:.1 is 80% or more and which is an amino acid sequence of a protein having an ability of inhibiting the transcription of a type-I collagen gene;
(d) an amino acid sequence encoded by a DNA having a nucleotide sequence whose sequence identity with a DNA having a nucleotide sequence encoding the amino acid sequence represented by SEQ ID No:.1 is 90% or more and which is an amino acid sequence of a protein having an ability of inhibiting the transcription of a type-I collagen gene; and,
(e) an amino acid sequence encoded by a DNA capable of being hybridized under a stringent condition with a DNA having a nucleotide sequence encoding the amino acid sequence represented by SEQ ID No:.1 and which is an amino acid sequence of a protein having an ability of inhibiting the transcription of a type-I collagen gene; wherein said active ingredient is formulated with a pharmaceutically acceptable carrier.

In this context, the expressions "deletion, addition or substitution of at least one amino acid" in paragraph (b) descried above, "sequence identity . . . is 80% or more" in paragraph (c) and "sequence identity . . . is 90% or more" in paragraph (d) include a naturally-occurring variation resulting from a intracellular processing exerted onto a protein having the amino acid sequence represented by SEQ ID No:.1 or from the difference between species, individuals, organs or tissues from which such protein is derived as well as an artificial variation in an amino acid (for example a variation in an amino acid which exists in an amino acid sequence possessed by a protein which is produced by introducing the variation into a DNA encoding a naturally-occurring protein by means of a site-specific variation introducing method or a mutagenic treatment followed by expressing such variation).

A method by which the "deletion, addition or substitution of at least one amino acid" (hereinafter referred together as modification of an amino acid) in paragraph (b) descried above is effected artificially may for example be a method in which a conventional site-specific variation transduction is applied to a DNA encoding the amino acid sequence represented by SEQ ID No:. 1 and then this DNA is expressed by a conventional method. Such site-specific variation-introducing method employed here may for example be a method utilizing an amber variation (Gapped duplex method, Nucleic Acids Res., 12, 9441-9456 (1984)) or a PCR method using a variation introducing primer.

The number of the amino acids which are modified as described above is at least one residue, typically 1 or several ("several" referred herein means 2 to about 10) residues or more. Such number of the modifications may be any number within a range which allows the ability of inhibiting the transcription of a type-I collagen gene to be detected.

Among the deletion, addition or substitution described above, the substitution of an amino acid is an especially preferred mode of the modification. Such substitution is preferably a substitution with an amino acid which is analogous characteristically with regard to the hydrophobicity, the electric charge, the pK and the steric configuration. Such substitution may for example be a substitution within a group of [1] glycine, alanine; [2] valine, isoleucine, leucine; [3] aspartic acid, glutamic acid, asparagine, glutamine; [4] serine, threonine; [5] lysine, arginine; and [6] phenylalanine, tyrosine.

In the present invention, the term "sequence identity" means an identity and a homology in the sequence between two DNAs or two proteins. Such "sequence identity" may be determined by comparing two sequences aligned optimally over the entire region of the sequence to be compared. A DNA or protein to be compared here may has an addition or deletion (for example, a gap) in the optimal alignment of the two sequences. Such sequence identity may be calculated for example by obtaining an alignment utilizing a Clustal W algorithm (Nucleic Acid Res., 22 (22): 4673-4680 (1994)) using Vector NTI. The sequence identity may be determined by a sequence analyzing software, typically Vector NTI, GENETYX-MAC or a public database-presented analysis tool. Such public database may commonly be utilized for example at URL http://www.ddbj.nig.ac.jp..

The sequence identity in the present invention is preferably 80% or more, for example, on the basis of an amino acid sequence, and 90% or more on the basis of a nucleotide sequence. It is a matter of course that a sequence identity whose identity in the 52nd to 130th amino acid sequence in the amino acid sequence represented by SEQ ID No:.1 is substantially almost 100% and whose identity in the 1st to 51st amino acid sequence is 50% or more may be acceptable.

With regard to the expression "capable of being hybridized under a stringent condition" in paragraph (e) described above, the hybridization employed here may be performed in accordance with a conventional method described for example in Sambrook J., Frisch E. F., Maniatis T., Molecular Cloning 2nd edition, Cold Spring Harbor Laboratory Press. The term "stringent condition" may for example be a condition in which a hybrid is formed at 45° C. in a solution containing 6×SSC (10×SSC corresponds to a solution containing 1.5 M NaCl, 0.15 M trisodium citrate) and then washed at 50° C. with 2×SSC (Molecular Biology, John Wiley & Sons, N.Y. (1989), 6,3,1-6,3,6). The salt concentration in a washing step may be selected within the range from 2×SSC at 50° C. (condition of low stringency) to 0.2×SSC at 50° C. (condition of high stringency). The temperature in the washing step may for example be room temperature (condition of low stringency) to 65° C. (condition of high stringency). It is also possible to change both of the salt concentration and the temperature.

Among the proteins of the present invention, a DNA-binding protein having the amino acid sequence represented by SEQ ID No:. 1 is known as a human-derived YB-1 (GenBank Accession No.M24070).

Such protein may be searched for as described below.

For example, a collagen accumulation quantity is analyzed by a method comprising (1) a first step for bringing a test protein into contact with a cell having a type-I collagen gene and (2) a second step, following to the first step, for determining the collagen accumulation quantity. In this procedure, the difference is detected by comparing the collagen accumulation quantities in the groups each of which employed different two or more proteins independently as test proteins (first accumulation quantity, second accumulation quantity). Based on the difference thus detected (difference between the first accumulation quantity and the second accumulation quantity), the type-I collagen gene transcription regulating ability of the test protein described above is evaluated. Thus, the search is accomplished by selecting a protein having an ability of inhibiting the transcription of a type-I collagen gene thus evaluated. It is a matter of course that the monitoring of the expression level of a reporter gene as described below in a searching method (III) of the present invention may also be employed instead of the analysis of the collagen accumulation quantity in the second step described above to search for a protein having an ability of inhibiting the transcription of a type-I collagen gene.

In a method described above, a protein having no ability of inhibiting the transcription of a type-I collagen gene may be employed as at least one of the protein among the two or more different proteins described above to evaluate the ability of inhibiting the transcription of the type-I collagen gene possessed by the other test protein, or an ability of inhibiting the transcription of the type-I collagen gene possessed by at least one protein among the two or more different proteins described above may be employed as a basis for evaluating the ability of inhibiting the transcription of the type-I collagen gene possessed by the other test protein.

The protein of the present invention preferably has a molecular weight, as determined by SDS-PAGE, of about 40 kDa to about 60 kDa, especially, about 50 kDa (for instance, which is equivalent to that of a protein having an amino acid sequence represented by SEQ ID NO:1), in the cases where the protein of the present invention is that having no modification of an amino acid(s) or that having a small scale of modification of an amino acid(s). On the other hand, the protein of the present invention preferably has a molecular weight, as determined by SDS-PAGE, of about 10 kDa to about 40 kDa, especially, about 20 kDa (for instance, which is equivalent to that of a protein having an amino acid sequence from the 1st amino acid to the 129th amino acid of the amino acid sequence represented by SEQ ID NO:1), in the cases where the protein of the present invention is that having a large scale of modification of amino acids.

A method for preparing the protein of the present invention (including a method for preparing a gene encoding said protein) is described below.

First a gene encoding the protein of the present invention (hereinafter sometimes referred to as the gene of the present invention), such as, for example, (a) a DNA having a nucleotide sequence encoding the amino acid sequence represented by SEQ ID No:.1;

(b) a DNA having a nucleotide sequence encoding an amino acid sequence which is formed as a result of the deletion, addition or substitution of at least one amino acid in the amino acid sequence represented by SEQ ID No:.1 and which is an amino acid sequence of a protein having an ability of inhibiting the transcription of a type-I collagen gene;

(c) a DNA which has a nucleotide sequence encoding an amino acid sequence whose sequence identity with the amino acid sequence represented by SEQ ID No:.1 is 80% or more and which has a nucleotide sequence encoding an amino acid sequence of a protein having an ability of inhibiting the transcription of a type-I collagen gene;

(d) a DNA having a nucleotide sequence whose sequence identity with a DNA having a nucleotide sequence encoding the amino acid sequence represented by SEQ ID No:.1 is 90% or more and which is a nucleotide sequence encoding an amino acid sequence of a protein having an ability of inhibiting the transcription of a type-I collagen gene; and, (e) a DNA capable of being hybridized under a stringent condition with a DNA having a nucleotide sequence encoding the amino acid sequence represented by SEQ ID No:.1 and which is a nucleotide sequence encoding an amino acid sequence of a protein having an ability of inhibiting the transcription of a type-I collagen gene; is obtained in accordance with a conventional gene engineering method (for example a method described in Sambrook, J., Frisch E. F., Maniatis T., Molecular Cloning 2nd edition, Cold Spring Harbor Laboratory Press). Subsequently, the resultant gene of the present invention is employed to produce and obtain the protein of the present invention in accordance with a conventional gene engineering method. Thus, the protein of the present invention may be prepared.

Typically, a RNA is prepared, for example, from a human tissue or cell, or a cell culture prepared therefrom. For example, a normal human fetal dermal fibroblast is pelletized in a solution containing a potent protein denaturant such as guanidine hydrochloride or guanidine thiocyanate and then the pelletized material is combined with phenol or chloroform to denaturalize the protein. After removing the denaturalized protein for example by a centrifugation, the supernatant recovered is subjected to a guanidine hydrochloride/phenol method, an SDS-phenol method, a guanidine thiocyanate/CsCl method and the like to extract the total RNA. Commercial reagents for these methods include ISOGEN (NIPPON GENE), TRIZOL reagent (Gibco BRL) and the like.

The total RNA thus obtained is used as a template to anneal an oligo dT primer with a polyA sequence of an RNA and treated with a reverse transcriptase, whereby synthesizing a single-stranded cDNA. Subsequently, this single-stranded cDNA is used as a template together with a primer which is an oligonucleotide designed based on a nucleotide sequence encoding the amino acid sequence of the protein of the present invention (for example, a nucleotide sequence encoding the amino acid sequence represented by SEQ ID NO:1 or a nucleotide sequence represented by SEQ ID NO:26) to perform a polymerase chain reaction (hereinafter abbreviated as PCR), whereby amplifying and obtaining the gene of the present invention.

This single-stranded cDNA is employed as a template and reacted in the presence of a DNA polymerase, whereby synthesizing a double-stranded cDNA. A double-stranded cDNA thus obtained is inserted, for example, into a vector such as plasmid pUC 118 or phage λgt10, whereby preparing a cDNA library. From the cDNA library thus obtained or a commercial cDNA library, the gene of the present invention may be obtained by a hybridization using as a probe a DNA having a partial nucleotide sequence of a nucleotide sequence encoding the amino acid sequence of the protein of the present invention (for example, a nucleotide sequence encoding the amino acid sequence represented by SEQ ID NO:1 or a nucleotide sequence represented by SEQ ID NO:26), or by a PCR using as a primer an oligonucleotide designed based on a nucleotide sequence encoding the amino acid sequence of the protein of the present invention (for example, a nucleotide sequence encoding the amino acid sequence represented by SEQ ID NO:1 or a nucleotide sequence represented by SEQ ID NO:26).

A primer used in a PCR may be obtained by selecting a nucleotide sequence having a length of about 20 bp to about 50 bp and having a % G or C base of about 40% to about 60% from known nucleotide sequences encoding the protein of the present invention described above and then designing and synthesizing an oligonucleotide based on this nucleotide sequence. Typically, a human gene of the present invention may be obtained by using the oligonucleotide consisting of the nucleotide sequence represented by SEQ ID No:.5 as a forward primer and the oligonucleotide consisting of the nucleotide sequence represented by SEQ ID No:.6 as a reverse primer.

The nucleotide sequence of the gene of the present invention thus obtained may be identified by Maxam Gilbert method (described for example in Maxam, A. M.& W. Gilbert, Proc. Natl. Acad. Sci. USA, 74, 560, 1977) or Sanger method (described for example in Sanger, F. & A. R. Coulson, J. Mol. Biol., 94, 441, 1975, Sanger, F. & Nicklen and A. R. Coulson, Proc. Natl. Acad. Sci. USA, 74, 5463, 1977).

Thus, a polynucleotide encoding a DNA-binding protein which is an active ingredient of the accumulation inhibitor (II) of the present invention employed for inhibiting a collagen accumulation (especially for inhibiting the transcription of a type-I collagen gene) may be prepared.

The gene of the present invention may be cloned into a vector in accordance with a conventional gene engineering method described for example in Sambrook J., Frisch E. F., Maniatis T., Molecular Cloning 2nd edition, Cold Spring Harbor Laboratory Press (1989).

A vector may for example be plasmid pUC 119 (TAKARA) or phagimid pBluescriptII (STRATAGENE) when *E.coli* is employed as a host cell. When budding yeast is employed as a host cell, plasmid pACT2 (Clontech) may be exemplified. When a mammalian cell is employed as a host cell, those which may be exemplified are a plasmid such as pRC/RSV, pRC/CMV (Invitrogen), a vector containing an autonomous replication starting point derived from a virus such as bovine papilloma virus plasmid pBPV (AMERSHAM PHARMACIA) and EB virus plasmid pCEP4 (Invitrogen) as well as a virus such as vaccinia virus. When an insectival animal cell (hereinafter referred to as insect cell) is employed as a host cell, an insect virus such as vaculovirus may be exemplified.

A promoter capable of functioning in a host cell is bound upstream of the gene of the present invention in a functional form, which is then integrated into a vector described above, whereby constructing an expression vector capable of expressing the gene of the present invention in the host cell. To be "bound . . . in a functional form" referred here means that the gene of the present invention, upon being transduced into a host cell, is bound to a promoter so that it is expressed under the regulation by said promoter in the host cell. A promoter capable of functioning in a host cell, when *E. coli* is a host cell, may for example be an *E. coli*'s promoter of the lactose operon (lacP), promoter of tryptophan operon (trpP), promoter of arginine operon (argP), promoter of galactose operon (galP), a synthetic promoter functional in *E. coli* such as tac promoter or trc promoter, T7 promoter, T3 promoter, λ phage promoters (λ-pL, λ-pR) and the like. When the host cell is an animal cell or fission yeast, Rous Sarcoma virus (RSV) promoter, cytomegalovirus (CMV) promoter, an early or late promoter of Simian virus (SV40) and Mouse mammary tumor virus (MMTV) promoter may be exemplified. When the host cell is a budding yeast, an ADH1 promoter (the ADH1 promoter may be prepared by a conventional gene engineering method from an yeast expression vector pAAH5 having an ADH1 promoter and the terminator thereof [available from Washington Research Fundation, Ammerer et al., Method in Enzymology, 101 part (p192-201)]. The ADH1 promoter is encompassed in U.S. patent application Ser. No. 299,733 by Washington Research Foundation, and its industrial or commercial use in United States may require an approval by the right-holder.) may be exemplified.

Generally, a DNA formed by ligating a promoter functional in a host cell to the gene of the present invention in a functional form is integrated into a vector capable of being utilized in the host cell, which is then transduced in the host cell. When using a vector which originally has a promoter functional in a host cell, the gene of the present invention may be inserted downstream of said promoter in such a manner that the promoter possessed by the vector is bound to the gene of the present invention in a functional form. For example, plasmid pRC/RSV or pRC/CMV described above is provided with a cloning site downstream of the promoter functional in an animal cell, and, into this cloning site, the gene of the present invention is inserted and then transduced into an animal cell, whereby expressing the gene of the present invention. In the case of plasmid pACT2 for an yeast described above which has an ADH1 promoter, the gene of the present invention is inserted downstream of the ADH1 promoter of this plasmid or a derivative thereof, whereby constructing an expression vector capable of expressing the gene of the present invention in budding yeast such as CG1945 (Clontech). A vector having a marker gene (for example, an antibiotic resistance-imparting gene such as kanamycin-resistant gene, neomycin-resistant gene) may advantageously be used when a transformant into which the gene of the present invention has been transduced is selected using the phenotype of this marker gene as an index.

When a further higher expression should be achieved, a ribosome-binding region may be ligated upstream of a gene encoding the protein of the present invention. Such ribosome-binding region employed may for example be those described in Guarente L. et al. (Cell 20, p543) or Taniguchi et al (Genetics of Industrial Microorganisms, p202, KODANSHA).

A method for transducing a vector into which the gene of the present invention has been integrated (hereinafter sometimes referred to as the vector of the present invention) into a host cell may be a conventional method suitable for the host cell. For example, when E. coli is employed as a host cell, a conventional method such as a calcium chloride method or an electroporation method described in "Molecular Cloning" (Sambrook J. et al., Cold Spring Harbor, 1989) is employed to transduce the vector of the present invention into the host cell. When a mammalian cell or an insect cell is employed as a host cell, a conventional gene transduction method such as a calcium phosphate method, a DEAE dextran method, an electroporation method or a lipofection method may be employed to transduce the vector of the present invention into the host cell. When an yeast cell is employed as a host cell, the transduction may be effected for example using an yeast transformation kit (Clontech) on the basis of a lithium method.

In order to select a transformant into which the vector of the present invention has been transduced, a marker gene described below is transduced into the host cell simultaneously with the gene of the present invention and then the host cell into which the vector of the present invention has been transduced is incubated by a method suitable for the characteristics of the marker gene transduced. For example, when such marker gene is a gene which gives a drug resistance against a screening agent exerting a lethal activity to the host cell (drug resistance-imparting gene), a culture medium containing such agent is employed to incubate the host cell into which the vector of the present invention has been transduced. The combination of a drug resistance-imparting gene and a screening agent may for example be the combination of a neomycin resistance-imparting gene and neomycin, the combination of a hygromycin resistance-imparting gene and hygromycin, the combination of blasticidin S resistance-imparting gene and blasticidin S and the like. When such marker gene is a gene which compensates the auxotrophy of the host cell, a minimal medium containing no respective nutrition is employed to incubate the cell into which the vector of the present invention has been transduced.

A resultant transformant into which the vector of the present invention has been transduced (hereinafter sometimes referred to as the transformant of the present invention) is incubated, whereby producing the protein of the present invention encoded by this gene.

For example, when the transformant of the present invention is a microorganism, the transformant is incubated usually in a medium containing suitable amounts of carbon sources, nitrogen sources and organic or inorganic salts employed generally for incubating a microorganism. The pH of the medium is usually about 6 to about 8. The incubation is performed in accordance with a conventional method in an ordinary microorganism such as a solid incubation and a liquid incubation (test tube shaking incubation, reciprocal shaking incubation, jar fermentation, tank incubation and the like). While the incubation temperature may vary within the range allowing a microorganism to be grown, it is usually about 15° C. to about 40° C. The incubation temperature may vary depending on various incubation parameters, and it is usually about 1 to 5 days. When an expression vector of an induction type, such as a temperature shift type or an IPTG induction type, the induction time period is preferably within 1 day, usually several hours.

When the transformant of the present invention is an animal cell of a mammal or an insect, the transformant may be incubated using a culture medium employed for incubating an ordinary cell culture. When using a screening agent for selecting the transformant of the present invention, the incubation is conducted preferably in the presence of such screening agent. In a case of a mammalian animal cell, D-MEM medium (NISSUI) supplemented with FBS at the final concentration of 10% may for example be employed and the incubation is continued at 37° C. in the presence of 5% $CO_2$ with replacing the medium with a fresh one every several days. Upon a confluent growth of the cell, the cell is individualized by dispersing in about 0.25 (w/v) % trypsin PBS solution to obtain a cell suspension, which is then diluted by several times and inoculated into a fresh petri dish, whereby obtaining a subculture. Also in a case of an insect cell, a culture medium for an insect cell such as a Grace's medium containing 10 (v/v) % FBS and 2 (w/v) % yeastlate is employed to incubate at a temperature of about 25° C. to about 35° C.

The protein of the present invention produced by incubating the transformant of the present invention may be recovered by an appropriate combination of ordinary methods for isolating and purifying a protein. For example, after completion of an incubation, the cell of the transformant of the present invention is collected for example by a centrifugation, suspended in a buffer solution if necessary, and pelletized by POLYTRON, an ultrasonic treatment, *DOWNS* homogenizer, and the like. A pellet suspension thus obtained is subjected to a centrifugation or a membrane filtration to remove insolubles to prepare a cell-free extract, which is subjected to a chromatography such as an ion exchange, hydrophobic, gel filtration or affinity chromatography, whereby purifying the protein of the present invention. In this procedure, a fraction containing the protein of the present invention may be identified for example by a DNA-binding assay using as a probe an oligonucleotide whose length is about 20 to about 200 bases containing a nucleotide sequence possessed by a DNA to which the protein of the present invention binds (for example a YB-1-binding sequence in Examples described below). Alternatively, the protein of the present invention is expressed as being fused at its N or C terminal with an amino acid sequence of consecutive 6 to 10 histidine residues and subjected to a chelate chromatography using a metal chelate resin, whereby accomplishing a one-step purification.

A DNA-binding protein serving as an active ingredient of the accumulation inhibitor (I) of the present invention may thus be prepared.

The accumulation inhibitor (I) of the present invention may be administered in an effective amount orally or parenterally to a mammal such as a human. For example, the accumulation inhibitor (I) of the present invention may orally be administered in an ordinary dosage form such as a tablet, capsule, syrup, suspension and the like. The accumulation inhibitor (I) of the present invention may also be given parenterally by injection (subcutaneous, intravenous and the like), percutaneous or rectal administration and the like. Such suitable dosage form described above may be produced for example by incorporating the protein of the present invention into an ordinary carrier such as an excipient, binder, stabilizer, diluent and the like. If necessary, auxiliary agents such as a disintegrant, surfactant, lubricant, flowability-imparting agent, preservative, colorant, flavor, humectant, antiseptic, antioxidant and the like may also be incorporated. A formulation for injection may be produced by incorporating the protein of the present invention into a pharmaceutically acceptable carrier such as an aqueous solvent, non-aqueous solvent, buffer, solubilizing aid, osmotic agent, stabilizer and the like. If necessary, auxiliary agents such as an antiseptic, suspending agent, emulsifier and the like may also be incorporated. For a parenteral administration, the accumulation inhibitor (I) of the present invention may be used in a form of an ordinary liquid or lotion formulation such as a solution, emulsion or suspension or a semi-solid formulation such as an ointment, percutaneous gel absorbent and the like. Alternatively, a sustained-release formulation employing as a carrier a sustained-release polymer (for example a formulation of the accumulation inhibitor (I) of the present invention impregnated in a pellet of a polymer of ethylene vinyl acetate, which is implanted surgically into a tissue to be treated) may also be employed.

The dose may vary depending on various factors such as age, sex, body weight of a mammal to be treated, the severity of the disease, the types of the inventive fat accumulation inhibitor employed as well as the administration mode, and is usually about 1 mg to about 2 g, preferably about 5 mg to about 1 g, per oral as an active ingredient daily in an adult, and about 0.1 mg to about 500 mg as an active ingredient when given by an injection to an adult. Such daily dose may be given all at once or as being divided into several portions.

A disease indicated for the accumulation inhibitor (I) of the present invention may for example be liver cirrhosis, interstitial pulmonary disease, chronic renal insufficiency (or a disease leading to a chronic renal insufficiency), post-inflammatory hyperplastic scar, postoperative scar or burn scar, or scleroderma, arteriosclerosis, hypertension, rheumatoid arthritis and other diseases induced by an excessive integration of a collagen (for example fibrosis).

The polynucleotide for coding the protein of the present invention, that is the gene on the present invention, serving as an active ingredient of the accumulation inhibitor (II) of the present invention, may be prepared in the manner previously described. The polynucleotide, however, may also be used in the form of a recombinant vector or a recombinant virus containing the polynucleotide. Examples of such forms include virus vectors such as a retrovirus vector, an adenovirus vector, an adeno-associated vector, a herpes simplex virus vector, an SV40 vector, a polyoma virus vector, a papilloma virus vector, a picornavirus vector, and a vaccinia virus vector. Furthermore, when using an adenovirus vector, it is also possible, for example, to produce, collect and then use a recombinant virus, which is produced by incorporating the gene of the present invention to a multi-cloning site of Transfer Vector using an AdEasy Kit manufactured by QUANTUM, followed by straightening the resulting recombinant vector, followed by transforming the vector together with a pAdEasy vector to an *Escherichia coli* to incorporate a homologous recombinant DNA to a human 293A cell.

Moreover, it is also possible to use non-viral vectors such as a plasmid DNA having a promoter/enhancer region of a human cytomegalovirus. In systems in which the gene of the present invention is delivered locally using a non-viral vector, for example, in the case where the gene of the present invention is injected directly to a fibrosed tissue site, the plasmid DNA is very useful. The employment of a method of introducing an expression vector into a cell taken out of the body and then returning the cell to the inside of the body, i.e., the ex vivo method, may make all known introductory procedures available. A non-viral vector may be transduced by, for example, a) direct injection, b) transduction through liposomes, c) cell transfection by a calcium phosphate method, an electroporation method, and a DEAE-dextran method, and d) delivery through polybrene, e) protoplast fusion, f) microinjection and g) transduction through polylysine.

The accumulation inhibitor (II) of the present invention may be administered parenterally in its effective dose to mammals such as humans. Examples of such parenteral administration include the above-mentioned injections (subcutaneous injections, intravenous injections, etc.) Formulation for the above-mentioned suitable administration may be manufactured by incorporating the gene of the present invention (including the form of the gene of the present invention of the vector, virus, or plasmid type) to pharmacologically acceptable carriers such as water-soluble solvents, water-insoluble solvents, buffer agents, solubilizers, isotonizing agents and stabilizers. Adjuvants such as preservatives, suspending agents and emulsifiers may be added, if needed. Moreover, in parenteral administration, the accumulation inhibitor (II) of the present invention may be used in the form of a conventional liquid formulation such as a solution.

The dose of the accumulation inhibitor (II) varies depending upon the age, sex, weight or degree of disease of the mammals to which the agent is administered and upon the type and administration form of the accumulation inhibitor (I). In usual, however, it may be administered in an active ingredient amount such that a level of the protein of the present invention in cells equal to that achieved in the case where the accumulation inhibitor (I) of the present invention is administered to patient cells. Moreover, the accumulation inhibitor (II) of the invention of said daily dose may be administered in one stage or in several stages.

Examples of the diseases to which the accumulation inhibitor (II) of the present invention may be applied include excessive accumulation of a collagen (for example, fibrosis) such as liver cirrhosis, interstitial pulmonary diseases, chronic renal insufficiency (or a disease leading to a chronic renal insufficiency), post-inflammatory hyperplastic scar, postoperative scar or burn scar, scleroderma, arteriosclerosis, hypertension, and rheumatoid arthritis.

The present invention also provides a method for inhibiting a collagen accumulation in mammals [the accumulation inhibiting method (I) of the present invention] comprising a step for providing an exogenous gene encoding the protein of the present invention to a mammalian cell so that said exogenous gene is located in a position enabling its expression in said cell.

The mammalian cell may be a cell derived from mammals such as humans, monkeys, mice, rats and hamsters. The cell may be that separated from the tissue, that forming a group having the same function or gestalt, and that present inside the bodies of the above-mentioned mammals.

Therefore, by the "mammalian cell" is meant, in the case where the mammals are humans, from humans applied with generally-called gene therapy to established cell lines such as those used for various experiments, and also is meant, in the case where the mammals are non-human animals, from non-human animals applied with generally-called gene therapy to model animals or established cell lines such as those used for various experiments. In the latter case, desirable animal species include rats, mice and the like.

The exogenous gene for coding the protein of the present invention may be prepared by procedures similar to that previously described in "A method for preparing the protein of the present invention (including a method for preparing a gene encoding said protein)".

By preparing a transformed cell in the manner described later using the thus prepared exogenous gene, a transformed cell may be obtained which has the exogenous gene provided so that said exogenous gene is located in a position enabling its expression in said cell.

The phrase "is located in a position enabling its expression" used for the accumulation inhibiting method (I) of the present invention means that a DNA molecule is placed in a position adjoining a DNA sequence directed to the transcription and translation of the nucleotide sequence of the DNA molecule (that is, for example, a DNA sequence which promotes the production of the protein of the present invention or RNA molecules thereof).

The expression level of the gene of the protein of the present invention should be at least that sufficient to inhibit collagen accumulation as compared with cells having no gene of the protein of the present invention transduced. In this case, the exogenous gene for coding the protein of the present invention may also be an exogenous gene for coding the entire or a part of the protein of the present invention.

In the above-mentioned collagen accumulation inhibiting method, the collagen accumulation may be inhibited by the preparation of a transformed cell having an exogenous gene for coding the protein of the present invention incorporated in a genome.

In the above-mentioned collagen accumulation inhibiting method, it is recommended to use, as a gene construct (hereinafter, referred sometimes to as the gene construct of the present invention) or gene migration arrival means used for the introduction of an exogenous gene for coding the protein of the present invention into a mammalian cell, retroviral vectors, adenovirus vectors, adeno-associated vectors or other virus vectors, which have affinities to the mammalian cell into which the exogenous gene will be transduced. Examples thereof include known vectors disclosed in Miller, Human Gene Therapy, 15-14, 1990; Friedman, Science, 244; 1275-1281, 1989; Eglitis and Anderson, Bio Techniques, 6:608-614, 1988; Tolstoshev and Anderson, Current Opinion in Biotechnology 1, 55-61, 1990: Sharp, The Lancet, 337: 1277-1278, 1991; Cornetta et al., Nucleic Acid Research and Molecular Biology, 36:311-322, 1987; Anderson, Science, 22: 401-409, 1984; Moen, Blood Cells, 17:407-416, 1991; Miller et al., Biotechniques 7:980-990, 1989; Le Gai La Salle et al., Science, 259:988-990, 1993; and Johnson, Chest, 107: 77S-83S, 1995. Retroviral vectors disclosed in Rosenberg et al., N. Engl. J. Med, 323: 370, 1990; Anderson et al., U.S. Pat. No. 5,399,346, etc. are particularly well developed and have been used in clinical settings. For example, when the cell is an animal cell, an SV40 virus promoter, a cytomegalovirus promoter (CMV promoter), a Raus Sarcoma Virus promoter (RSV promoter), β actin gene promoter, an aP2 gene promoter, etc. are mentioned. It is also possible to utilize commercially available vectors having such promoters upstream from their multi-cloning sites.

The exogenous gene may be put under the control of a promoter that causes the gene of the protein of the present invention to be expressed constructively. The exogenous gene may also be put under the control of a promoter that regulates the expression of the gene of the protein of the present invention by environmental stimulus. For example, the exogenous gene may be expressed using tissue-specific or cell-type specific promoters or promoters which will be activated by chemical signals, external signals such as agents or the introduction of agents.

Moreover, in order to transduce an exogenous gene (DNA) for coding the protein of the present invention into cells expected to have excessive accumulation of collagen if it is left as it is, non-viral approaches may also be employed. Such approaches are exemplified by asialorosonucoid-polylysine conjugation disclosed in Felgner et al., Proc. Natl. Acad. Sci. USA 84:7413, 1987; Ono et al., Neurosci. Lett 117:259, 1990; Brigham et al., Am. J. Med. Sci. 298:278, 1989; Staubinger et al., Meth. Enz. 101:512, 1983; lipofection disclosed in Wu et al., J. Biol. Chem. 263:14621, 1988; Wu et al., J. Biol. Chem. 264:16985, 1989; microinjection disclosed in Wolff et al., Science 247:1465, 1990, a calcium phosphate method, a DEAE dextran method, an electroporation method, a protoplast fusion method and a liposome method.

For any of the above approaches, the gene construct of the present invention is preferably applied (for example, by injection) to the site where the excessive collagen accumulation is expected to occur, but may also be applied to tissue in the vicinity of the site where phenomena such as the excessive collagen accumulation are expected to occur or to a blood vessel to the cells where the excessive collagen accumulation is expected to occur.

In the gene construct of the present invention, the expression of the gene (cDNA) of the protein of the present invention may be directed to any suitable promoter (e.g., human cytomegalovirus (CMV), simian virus 40 (SV40), or metallothionein promoters), and it may be regulated by any desired mammalian regulatory element. For example, if desired, enhancers known to direct preferential gene expression in neuronal cells, T cells or B cells may be used for the expression of the gene of the protein of the present invention. The enhancers include, without any limitations, those characterized in that their expression is specific for tissues or cells. Alternatively, when a clone of the gene (genome) of the protein of the present invention is utilized as a gene construct (for example, a clone of the genome of the protein of the present invention isolated through the hybridization with said gene (cDNA) of the protein of the present invention), the expression may also be regulated through a cognate regulatory sequence and, if needed, regulatory sequences derived from a heterologous source, e.g., any of the promoters or regulatory elements described above.

When the aforementioned collagen accumulation inhibiting method is applied as means for a gene therapy, the therapy is accomplished by direct administration of the gene (an mRNA or an antisense mRNA) of the protein of the present invention into cells. The mRNA to be used may be produced and isolated by any conventional technique, but is most readily produced by in vitro transcription using a gene (cDNA) of the protein of the present invention under the control of a high efficiency promoter (e.g., the T7 promoter). Administration of the gene (mRNA or antisense mRNA) of the protein of the present invention to cells may also be carried out by any of the methods for direct polynucleotide administration described above.

The above-mentioned collagen accumulation inhibiting method is also applicable as means of gene therapy, namely, the transplant of normal genes to patient's affected cells. In the use of such means, the transfection of the gene of normal one of the protein of the present inventions is carried out to the cell that is either exogenous or endogenous for the patient and that may be cultured. Subsequently, the transfected cell is serologically injected to a target tissue.

Ideally, the production of the protein of the present invention by any gene therapeutic approach results in a cellular level of the protein of the present invention that is at least equivalent to the cellular level of the normal one of the protein of the present inventions in non-affected cells.

As a method different than the aforementioned collagen accumulation inhibiting method, the protein of the present invention may be administered directly (for example, by injection) to a site where excessive collagen accumulation is expected to occur or be administered to all over the body (for example, by a conventional recombinant protein administration method). For example, the dose of the protein of the present invention varies depending upon various factors such as patient's conformation of body and health conditions, but usually is from 0.1 mg to 100 mg a day. The protein of the present invention is administered in a preparation being pharmaceutically acceptable.

The accumulation inhibiting method (I) of the present invention in the case where the mammal is a transformed mouse will be explained, as an example, in more detail below.

The method for introducing the gene of the present invention in the preparation of transformed mice may be exemplified by a microinjection method, a method using a retrovirus and a method using an embryonal stem cell (ES cell). Of these methods, the microinjection method is most widely used. The microinjection method is a method in which a solution containing an exogenous gene is injected into the pronucleus of a fertilized egg under a microscope using a micromanipulator.

First, the gene of the present invention is injected into a fertilized egg. In this stage, in order to incorporate the gene to a chromosome in a high probability, it is desirable to remove the vector region used for the isolation of the gene of the present invention as much as possible, to remove a region rich in AU which contribute to the destabilization of an mRNA, and to straighten. Furthermore, it is preferable to insert an intron in advance to the gene of the present invention. Such an intron may, for example, be β-globin intron, etc.

A fertilized egg is extracted from a mouse of a system meeting the purpose. Candidate mice include inbred C57BL/6 or C3H mice, mice hybridized from a C57BL/6 mouse and a mouse of another system (for example, (C57BL/6×DBA/2)F1, etc.) and outbred ICR mice. Fertilized eggs are usually obtained by mating a male mouse and a female mouse which has been made induce superovulation by intraperitoneal administration of both pregnant mare serum gonadotropin and human chorionic gonadotropin and thereafter extracting the eggs from the female mouse. The fertilized eggs may be stored until the injection of the gene of the present invention by charging it in a drop for cultivation and then culturing and maintaining it with a $CO_2$ gas incubator.

The injection of the gene of the present invention is performed under the inverted microscope having a micromanipulator. It is recommended to use a fertilized egg in a developmental stage ranging from the time when the male pronucleus becomes greater than the female pronucleus to the fusion of both pronucleus. A fertilized egg is fixed first and a DNA solution containing the gene of the present invention is injected into the male pronucleus of the fertilized egg. The DNA solution is, if needed, prepared as a complex. A substance to be used for the formation of a complex may be liposome, calcium phosphate, retrovirus and the like. Expansion of the male pronucleus confirms that the injection of the DNA solution has been done successfully. The amount of the DNA to be injected may, for example, be such an amount that about 200 to about 3000 copies of the gene of the present invention are contained.

After culturing the fertilized egg into which the gene of the present invention was injected until the fertilized egg becomes a blastocyst, it is transplanted to the uterus of a foster mother. It is preferable to transplant the fertilized egg to the oviduct of a foster mother immediately after the operation of injecting the gene of the present invention. It is recommended to use, as a foster mother, an ICR female mouse made pseudopregnant by mating with a vasectomized male mouse. Specifically, the skin and the muscularis near a kidney by the back side of the ICR female mouse are incised first, the ovary, an oviduct and a uterus are pulled out, an ovary film is torn, and an oviduct opening is discovered. Subsequently, the fertilized egg which survived after injection operation of the gene of the present invention is transduced through the oviduct opening and the ovary, the oviduct and the uterus are returned to the abdominal cavity. The muscularis is thereafter sutured and the skin is clipped. An offspring is produced after about 20 days.

A part of the body tissue of the offspring produced, for example a part of its tail, is cut off and the presence of the gene of the present invention is confirmed by the Southern blotting of the DNA extracted from the part. This may confirm that the gene of the present invention has been transduced to a non-human animal. Alternatively, other confirming methods such as a PCR may be used.

When using a transformed non-human animal constructed in such a manner is employed in the searching methods described later as cells in the body, the usual procedures may be used for the administration of a substance to be tested to the transformed non-human animal. For example, a procedure of mixing a substance to be tested to a feed or drinking water and a procedure of directly administering (for example, intravenous, intramuscular, intracutaneous, subcutaneous or peritoneal administrations) are mentioned. If needed, intrapreculture may be performed prior to the administration of a substance to be tested. The dose and administration term may be selected appropriately depending upon the type and age in week of the animal and the administration procedure to be adopted. For example, the substance to be tested may be administered for about two to four weeks by about 0.1 mg/kg-weight/day to about 10 mg/kg-weight/day in peritoneal administration for non-human animals such as rodent animals and by about 1 mg/kg-weight/day to about 100 mg/kg-weight/day in oral administration for non-human animals such as rodent animals.

In the above-mentioned procedures, it is also possible to provide the aforementioned exogenous gene under a condition allowing a positive regulatory factor of the collagen accumulation promoting pathway is to be present outside of said cell. In such a situation, preferred is, for example, a condition where a positive regulatory factor of the collagen accumulation promoting pathway is present outside the cell in an amount equivalent to that of the factor present in a body of a mammal which may be diagnosed as a disease caused by an excessive accumulation of a collagen described later, for example, in a body of a mammal which may be diagnosed to have a fibrosis.

The "positive regulatory factor of a collagen accumulation-promoting pathway" used herein means a substance that acts to activate transcription of collagen genes in a collagen synthesis mechanism the cell has. Examples thereof include a positive regulatory factor of a DNA bonding protein-dependent collagen accumulation promoting pathway.

Examples of said DNA bonding protein include AP-1 and Smad. Such proteins usually exist within cells and bond to expression regulatory regions present in the upstream regions of collagen genes through changing to their activated forms (phosphorylated states) triggered by extracellular stimulations. Such bonding activates transcription of the collagen genes.

Specifically, the positive regulatory factor of the collagen accumulation promoting pathway is exemplified by TGF-β.

The present invention also provides a method for inhibiting a collagen accumulation comprising a step for administering the protein of the present invention to a cell present in a body of a mammal which may be diagnosed to have a disease caused by an excessive accumulation of a collagen, for example, a cell present in a body of a mammal which may be diagnosed to have a fibrosis.

Examples of the diseases caused by the excessive accumulation of the collagen include excessive collagen accumulation diseases such as live cirrhosis, interstitial pulmonary diseases, chronic renal insufficiency (or a disease leading to a chronic renal insufficiency), post-inflammatory hyperplastic scar, postoperative scar or burn scar, scleroderma, arteriosclerosis, hypertension, rheumatoid arthritis and other diseases caused by an excessive accumulation of a collagen (for example fibrosis).

For "administering the protein of the present invention," it is possible to administer directly the protein of the present invention in the form of the aforementioned accumulation inhibitor (I) of the present invention, and alternatively, is possible to administer indirectly in the manner of the aforementioned accumulation inhibiting method (I) of the present invention. Moreover, in the latter case, it is recommended to administer the protein of the present invention so as, for example, to result in an intracellular level of the protein of the present invention equivalent to that in the former case.

The present invention also provides a method for inhibiting a collagen accumulation [the accumulation inhibiting method (II) of the present invention] comprising a step for administering the protein of the present invention to a mammalian cell under a condition allowing a positive regulatory factor of a collagen accumulation-promoting pathway to be present outside of said cell.

The "mammalian cell" and the "condition allowing a positive regulatory factor of a collagen accumulation-promoting pathway to be present outside of said cell" used herein are the same as those explained in the above-mentioned accumulation inhibiting method (I) of the present invention.

The present invention also provides a method for inhibiting a collagen accumulation [the accumulation inhibiting method (III) of the present invention] comprising a step for administering the protein of the present invention to a cell having a type-I collagen gene.

The "cell having a type-I collagen gene" used herein is a cell in which a sequential collagen synthesis mechanism works normally, the mechanism having transcription of the collagen gene, translation of an mRNA produced through the transcription, complex formation including change of a collagen protein produced through the translation to its matured form, and secretion of the matured collagen produced through the complex formation.

For administering the protein of the present invention to the cell, it is possible to administer directly the protein of the present invention in the form of the aforementioned accumulation inhibitor (I) of the present invention, and alternatively, is possible to administer indirectly in the manner of the aforementioned accumulation inhibiting method (I) of the present invention. Moreover, in the latter case, it is recommended to administer the protein of the present invention so as, for example, to result in an intracellular level of the protein of the present invention equivalent to that in the former case.

In this step, the concentration of the test substance, which is brought into contact with the cell having a type-I collagen gene, is only required, for example, to be about 0.1 μM to about 100 μM, and desirably from about 1 μM to about 50 μM. The time for keeping the cell and the test substance in contact is, for example, about one hour to about five days, and desirably from several hours to four days.

In the above-mentioned procedures, it is also possible to administer the protein of the present invention under a condition allowing a positive regulatory factor of the collagen accumulation promoting pathway to be present outside of said cell. The "condition allowing a positive regulatory factor of the collagen accumulation promoting pathway to be present outside of said cell" is the same as explained in the aforementioned accumulation inhibiting method (I) of the present invention.

The present invention also provides a method for searching for a substance which regulates the type-I collagen gene transcription regulating ability [the searching method (I) of the present invention], the method comprising:

(1) a first step for bringing a test substance into contact with a cell in expressing the protein of the present invention is to be expressed;

(2) a second step, following to said first step, for measuring the quantity of the protein of the present invention migrated into the nucleus of a cell or a parameter having a correlation with said quantity;

(3) a third step for evaluating type I collagen gene transcription regulating ability of said substance based on the quantity of the migrated protein or the parameter correlating with such quantity, which were determined in the second step; and (4) a fourth step for selecting a substance having the type-I collagen gene transcription regulating ability based on the type-I collagen gene transcription regulating ability evaluated in said step.

The quantity of the protein of the present invention migrated into the nucleus of a cell or parameter having a correlation with said quantity may be measured by separating a cell nucleus fraction by the usual procedure from the cell after being brought into contact with the test substance, followed by measuring the quantity of the protein of the present invention existing in the cell nucleus fraction separated or a parameter having a correlation with said quantity. In addition, for example, by separating the cell after being brought into contact with the test substance by the conventional procedure, followed by observing the separated cell with a fluorescence microscope or the like, the quantity of the (fluorescence-labeled) protein of the present invention existing in the cell nucleus or a (fluorescent) parameter having a correlation with said quantity may be determined.

A preferred example of the cell to be used in the measurement of the quantity of the protein of the present invention migrated into the nucleus of a cell may be a cell which expresses the protein of the present invention derived from humans. Moreover, an example of the cell to be used in the measurement of the parameter having a correlation with the quantity of the protein of the present invention migrated into the cell nucleus of the cell may be a cell which expresses an exogenous marker protein which enables to provide the parameter having a correlation with the quantity of the protein of the present invention migrated into the nucleus of a cell.

Specifically, exogenous marker proteins which may be employed include Green Fluorescent Protein (hereinafter, GFP) and the like.

For example, a cell is prepared which expresses a protein having both an amino acid sequence of the protein of the present invention and that of GFP. The cell is prepared by subjecting a DNA which codes the amino acid sequence of the protein of the present invention and contains no stop codon and a DNA which codes an amino acid sequence of GFP and contains no initiation codon to a PCR using as a primer an oligonucleotide prepared based on the nucleotide sequences of said DNAs. The DNA prepared is inserted in a vector so that the amino acid sequence of GFP is coded with their reading frames continued downstream from the amino acid sequence of the protein of the present invention and also that the DNA is expressibly connected to a promoter such as a Rous sarcoma virus (RSV) promoter and a cytomegalovirus (CMV) promoter. For example, it is also possible to employ a commercially available vector having said promoter and also having, downstream from the vector, both a gene insertion site and a nucleotide sequence for coding the amino acid sequence of GFP. By the introduction, to a cell such as a fibroblast, of a vector for expressing the thus obtained protein having both the amino acid sequence and that of GFP, a cell that can express the protein is obtained.

The obtained cell is cultured and is brought into contact with a test substance. The presence of fluorescence in the nucleus is detected through the observation of the cell with a fluorescence microscope using a FITC filter. When the quantity of the fluorescence in the nucleus of the cell which was brought into contact with the test substance is greater than the quantity of the fluorescence in a nucleus of a cell which was brought into contact only with a solvent (a control), the test substance is evaluated to have a type-(I) collagen gene transcription regulating ability (in this case, a transcription inhibiting ability).

The present invention also provides a method for searching for a substance which regulates a type-I collagen gene transcription regulating ability [the searching method (II) of the present invention], the method comprising:
(1) a first step for bringing two or more different test substances into contact independently with a cell which has a type-I collagen gene and in which an exogenous gene encoding the protein of the present invention so that said exogenous gene is located in a position enabling its expression in said cell;
(2) a second step, following to said first step, for monitering the collagen accumulation quantity independently;
(3) a third step for evaluating type-I collagen gene transcription regulating ability of said substance based on the difference served by comparing the collagen accumulation quantities, which were monitored independently in the second step, with each other; and
(4) a fourth step for selecting a substance having the type-I collagen gene transcription regulating ability based on the type-I collagen gene transcription regulating ability evaluated in said third step.

The "cell which has a type-I collagen gene and in which an exogenous gene encoding the protein of the present invention so that said exogenous gene is located in a position enabling its expression in said cell" is a cell obtained by subjecting a cell in which a sequential collagen synthesis mechanism works normally, the mechanism having transcription of the collagen gene, translation of an mRNA produced through the transcription, complex formation including change of a collagen protein produced through the translation to its matured form and secretion of the matured collagen produced through the complex formation, to a transformation through which the exogenous gene encoding the gene of the present invention is expressed, the transformation being similar to that conducted in the preparation of the transformed cell used in the aforementioned accumulation method (I) of the present invention. This cell is one in which the aforementioned sequential collagen synthesis mechanism does not work normally since, in the cell, the transcription of the collagen gene is inhibited by the protein of the present invention expressed in the cell. Accordingly, this type of cell may be utilized for searching for a substance having a type-I collagen gene transcription regulating ability through checking the change, caused by the action of the test substance, of the sequential collagen synthesis mechanism of the cell that the collagen synthesis mechanism recovers to function normally.

In the above-mentioned method, the first step may be conducted under a condition allowing a positive regulatory factor of a collagen accumulation-promoting pathway to be present outside of said cell. The "condition allowing a positive regulatory factor of a collagen accumulation-promoting pathway to present outside of the cell" is the same as that explained in the aforementioned accumulation inhibiting method (I) of the present invention.

The present invention also provides a method for searching for a substance which regulates the type-I collagen gene transcription regulating ability [the searching method (III) of the present invention], the method comprising:
(1) a first step for bringing a test substance into contact independently with each of (a) a cell containing a reporter gene which contains a nucleotide sequence required for initiating a transcription and which is ligated in a functional form to a type-I collagen gene expression regulating region and (b) a cell containing a reporter gene which contains a nucleotide sequence required for initiating a transcription and which is ligated in a functional form to a nucleotide sequence having no ability of binding to the protein of the present invention;
(2) a second step, following to said first step, for monitoring the reporter gene expression quantity independently;
(3) a third step for evaluating the type-I collagen gene transcription regulating ability of said substance based on the difference observed by comparing the expression quantities, which were independently in the second step, with each other; and
(4) a fourth step for selecting a substance having the type-I collagen gene transcription regulating ability based on the type-I collagen gene transcription regulating ability evaluated in said third step.

"(a) A reporter gene which contains a nucleotide sequence required for initiating a transcription and which is linked in a functional form to a type-I collagen gene expression regulatory region may be prepared, for example, by linking, in a functionable form, DNAs, respectively, having type-I collagen gene expression regulating region (that is, a nucleotide sequence having a bonding ability to the protein of the present invention), a nucleotide sequence required for initiating a transcription and a nucleotide sequence for coding a reporter protein so that these nucleotide sequences are arranged sequentially from the upstream.

The "nucleotide sequence of a type-I collagen gene expression regulating region" to be used for the reporting gene includes, for example, a nucleotide sequence of SEQ ID NO :2 and a nucleotide sequence (a nucleotide sequence of SEQ ID NO::3) of from −161 to −125 (+1 for the transcription starting point) in the promoter region of human collagen α2 (I) chain gene (COL1A2). When such a nucleotide sequence and the protein of the present invention are bound, the transcription of said reporter gene having the nucleotide sequence is inhibited.

Examples of the nucleotide sequence in which a "nucleotide sequence required for initiating a transcription" is arranged downstream from the "a type-I collagen gene expression regulating region" include a nucleotide sequence of the 5' upstream region of the human collagen α2 (I) chain gene (COL1A2) (for example, a region containing the base of No. −161 through the base of No. +57, wherein the transcription initiating point is numbered 1) (GenBank Accession No. J03464, Matrix Biol., 16:447, 1998). By linking a DNA having such a nucleotide sequence and a DNA having a nucleotide sequence for coding a reporter protein may be prepared a DNA of a reporter gene containing a type-I collagen gene expression regulating region, a nucleotide sequence required for initiating a transcription and a nucleotide sequence for coding a reporter protein (hereinafter, referred sometimes to as the reporter gene which accepts transcription regulation by the protein of the present invention).

"(b) A reporter gene which contains a nucleotide sequence required for initiating a transcription and which is ligated in a functional form to a nucleotide sequence having no ability of binding to the protein of the present invention" may be prepared, for example, by linking, in a functionable form, DNAs, respectively, having a nucleotide sequence having a bonding ability to the protein of the present invention, a nucleotide sequence required for initiating a transcription and a nucleotide sequence for coding a reporter protein so that these nucleotide sequences are arranged sequentially from the upstream.

Examples of the "nucleotide sequence having no ability of binding to the protein of the present invention" include nucleotide sequences resulting from substituting or deleting a part of the nucleotide sequence so as to extinguish their binding abilities to the protein of the present invention which the nucleotide sequence in said "type-I collagen gene expression regulating region" has. Specific examples include a nucleotide sequence of SEQ ID NO:25 and a nucleotide sequence of SEQ ID NO:4. The binding ability between a DNA having a predetermined nucleotide sequence and the protein of the present invention may be examined by the conventional methods such as Gel Shift Assay which detects the presence of the formation of a complex from a labeled DNA having the above-mentioned sequence and the protein of the present invention. Examples of the "nucleotide sequence required for initiating a transcription" include TATA boxes, etc. Specifically, a nucleotide sequence in the 5' upstream region of a thymidine kinase gene (tk) and the like may be mentioned. DNAs having such nucleotide sequences may be prepared by chemically synthesizing or amplifying and cloning by a polymerase chain reaction (hereinafter, PCR) and the like.

DNAs of reporter genes containing a nucleotide sequence showing no ability of binding to the protein of the present invention, a nucleotide sequence required for initiating a transcription and a nucleotide sequence for coding a reporter protein (hereinafter, referred sometimes to as a reporter gene which does not accept transcription regulation by the protein of the present invention) may be prepared in the same procedure as described above.

Preferred as the reporter protein which is coded to the "reporter gene" are proteins in which the measurement of the expression quantity of the protein or reporter gene based, for example, on the protein's enzyme activity becomes possible. For example, firefly luciferase, sea pansy luciferase, β-galactosidase, chloramphenicolacetyltransferase and alkaline phosphatase are mentioned. DNAs for coding such reporter proteins may be obtained, for example, by isolating the target DNAs through restriction enzyme digestion of DNAs of commercially available plasmids containing such DNAs.

The DNA containing a "reporter gene which does not accept transcription regulation by the protein of the present invention" and the DNA containing a "reporter gene which accepts transcription inhibition by the protein of the present invention" are incorporated separately to vectors such as plasmids. The resultant are transduced to cells by the conventional procedures such as a lipofection method, a DEAE dextran method, a calcium phosphate method and an electroporation method, and cells in which these reporter genes have been transduced are selected. Examples of the vectors include plasmids having replication origins and drug resistant genes which function in microorganisms suitable for genetic engineering technologies, such as *Escherichia coli*. In order to make it easy to select the cells having reporter genes transduced therein, it is also possible to transduce selection marker genes such as drug resistant genes simultaneously. Examples of drug resistant genes include a neomycin resistant (aminoglycosidephosphotransferase) gene, a blasticidin S resistant gene and a hygromycin resistant gene.

Examples of the above-mentioned cells include cells derived from mammals, and preferably cells derived from human tissues.

Specific examples include cells endogeneous to YB-1 gene such as human skin-derived fibroblasts are mentioned. Cells exogeneous to the protein of the present invention gene such as human glioblastoma cells may be employed, for example, after introducing DNAs for coding the protein of the present invention into the cells to express. The DNAs for coding the protein of the present invention may be transduced to cells simultaneously with DNAs containing the aforementioned reporter genes and may also be transduced separately. For example a DNA for coding human YB-1 may be prepared by designing and producing an oligonucleotide for amplifying the DNA based on a known nucleotide sequence (GenBank Accession No. M24070) and conducting a PCR using the prepared oligonucleotide as a primer. In the PCR, a commercially available human-derived cDNA may be used as a template. The resulting DNA for coding the protein of the present invention is inserted into a vector so as to be expressibly connected to a promoter such as a Rous sarcoma virus (RSV) promoter, a cytomegalovirus (CMV) promoter and an initial or late promoter of simian virus (SV40), thereby being transduced to a cell. A cell which expresses the protein of the present invention is then obtained. As the vector, for example, commercially available expression vectors having a promoter such as those described above and also having a site for gene insertion downstream from the promoter may be employed.

Next, a test substance is brought (independently) into contact with the cells (both cells) obtained in the procedure described above. In this step, the concentration of the test substance, which is brought into contact with the cells, is only required, for example, to be about 0.1 μM to about 100 μM, and desirably from 1 μM to 50 μM. The time for keeping the cells and the test substance in contact is, for example, from one hour to five days, and desirably approximately from several hours to four days.

After this step, the expression quantities of the reporter genes are monitored (independently). Although depending upon the types of the reporter proteins coded to the reporter genes used, the monitoring of the expression quantities of the reporter genes may generally be done by determining the quantities of the reporter proteins contained in cell extract solutions prepared by adding cytolytic agents to the cells to be examined. For example, when the reporter protein used has an enzyme activity, a substrate specific to the enzyme and a cell extract solution containing the enzyme are allowed to react, and then the quantity of the remaining substrate or the quantity of the reaction product and the quantity of the reporter protein are determined by using the quantity of luminescence, fluorescence absorbance, absorbance and the like as parameters. Specifically, for example, in the case of using luciferase as a reporter protein, when luciferin, which is a substrate of luciferase, and a cell extract solution are allowed to react, luminescence is observed in an intensity proportional to the quantity of the luciferase in the cell extract solution. Accordingly, it is possible to know the quantity of luciferase in the cell extract solution or the expression quantity of the luciferase gene by measuring the intensity of the luminescence with a measuring device such as a luminometer.

Next, the type-I collagen gene transcription regulating ability in the test substance is evaluated based on the difference observed by comparing (i) the reporter gene expression quantity resulting from the contact of the test substance and the cell having a reporter gene which accepts the transcription regulation by the protein of the present invention, and (ii) the reporter gene expression quantity resulting from the contact of the test substance and the cell having a reporter gene which does not accept the transcription regulation by the protein of the present invention, both being monitored in the aforementioned procedure. When the former expression quantity is less or greater than the latter expression quantity, the test substance can be evaluated to be a substance having a type-I collagen gene transcription regulating ability (when the former is less than the latter, a positive regulatory factor of the protein of the present invention-dependent collagen accumulation inhibiting pathway; when the former is greater than the latter, a negative regulatory factor of the protein of the present invention-dependent collagen accumulation inhibiting pathway) based on the collagen gene transcription regulating ability.

The substance having a type-I collagen gene transcription regulating ability may be selected under the tested type-I collagen gene transcription regulating ability in this way.

When more precise searching method is required, for example, a method described later is suitable. First, for a cell having a reporter gene which does not accept the transcription regulation by the protein of the present invention, the measured value of the expression quantity of the reporter gene in the case where it was contacted with the test substance is compared with the measured value of the expression quantity of the reporter gene in the case where it was contacted only with a solvent (a control). If both measured values are substantially the same, or specifically speaking, if the ratio of both measured values falls within the range of from about 0.9 to about 1.1, the test substance is selected temporarily for assaying the type-I collagen gene transcription regulating ability. When the ratio is, for example, less than about 0.9, there is a possibility that the test substance has some cytotoxicity. On the other hand, when the ratio, for example, exceeds about 1.1, there is the possibility that the test substance acts on the transcription regulation system not through the protein of the present invention. It is to be noted that the range of the ratio suitable for the selection of a test substance varies depending upon the characteristics of the cell to be used in the assay or measuring conditions and, therefore, is not limited to the above-cited values shown as examples.

Subsequently, for the cell having a reporter gene which accepts the transcription regulation by the protein of the present invention, the measured value of the expression quantity of the reporter gene in the case where it was contacted with the test substance temporarily selected as described above is compared with the measured value of the expression quantity of the reporter gene in the case where it was contacted only with a solvent (a control). If the measured value of the expression quantity of the reporter gene in the cell that was contacted with the test substance is less than the measured value of the cell which was contacted only with a solvent (a control), the test substance may be evaluated to be a positive regulatory factor of the protein of the present invention-dependent collagen accumulation inhibiting pathway. On the other hand, the measured value of the expression quantity of the reporter gene in the cell which was contacted with the test substance is greater than the measured value of the cell which was contacted only with a solvent (a control), the test substance may be evaluated to be a negative regulatory factor of the protein of the present invention-dependent collagen accumulation inhibiting pathway.

Of the aforementioned methods, a method is also permitted in which the first step is conducted under a condition allowing a positive regulatory factor of a collagen accumulation-promoting pathway to be present outside of said cell. The "condition allowing a positive regulatory factor of a collagen accumulation-promoting pathway to be present outside of said cell" is the same as that explained in the aforementioned accumulation inhibiting method (I).

Moreover, of the aforementioned methods, a method is also permitted in which the first step is conducted under a condition allowing a positive regulatory factor of the protein of the present invention-dependent collagen accumulation inhibiting pathway to be present inside of the cell. The positive regulatory factor of the protrin of the present invention-dependent collagen accumulation inhibiting pathway used herein means a substance that acts to inhibit transcription of collagen genes in a collagen synthesis mechanism the cell has. Examples of such a factor include the protein of the present invention itself.

It has become possible to provide the collagen accumulation inhibitor [the accumulation inhibitor (III) of the present invention] containing as an active ingredient a substance selected by the searching method or a pharmaceutically acceptable salt therof wherein said active ingredient is formulated with a pharmaceutically acceptable carrier.

In the accumulation inhibitor (III) of the present invention, it is possible to use salt as an active ingredient a compound represented by general formula (I) or a pharmaceutically acceptable salt thereof:

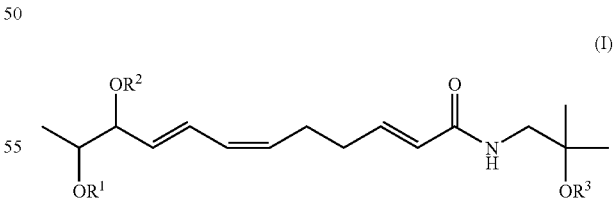

(I)

wherein $R^1$, $R^2$ and $R^3$ are same or different and each denotes a hydrogen atom, an alkyl group or an acyl group.

In the above general formula (I), examples of the alkyl groups represented by $R^1$, $R^2$, or $R^3$ include alkyl groups having 1-6 carbons, and specifically, a methyl group, an ethyl group, a n-propyl group, an isopropyl group, a n-butyl-group, an isobutyl group, a sec-butyl group, a tert-butyl group, a n-pentyl group, an isopentyl group, a neopentyl group, a 1,1-dimethylpropyl group, a 1-ethylpropyl group, a n-hexyl group, an isohexyl group, a 2-ethylbutyl group, a 1-methylpentyl group, a 1-ethylbutyl group, a 3-methylpentyl group, a 1,3-dimethylbutyl group etc.

Examples of the acyl groups represented by $R^1$, $R^2$, or $R^3$ include an acetyl group, a propionyl group, a butyryl group, an isobutyryl group, a valeryl group, an isovaleryl group, a pivaloyl group, etc.

The compound represented by said general formula (I) may be obtained by fractioning an ethanol extractant from a pericarp of angelica by applying it to thin-layer chromatography using silica gel, column chromatography using a reversed-phase column, high performance liquid chromatography, or the like or by converting in the conventional chemical synthesis procedure a compound refined from such a natural product. The measurement of mass spectrum, NMR spectrum or the like may confirm the chemical structure of the resulting compound.

The above-mentioned accumulation inhibitor (III) of the present invention contains as an active ingredient the compound represented by general formula (I) or a pharmaceutically-acceptable salt thereof, wherein said active ingredient is formulated with a pharmaceutically acceptable carrier.

In the accumulation inhibitor (III) of the present invention, at least one of the parts of a plant selected from the group consisting of angelica (*Zanthoxylum piperitum De Candolle*) and the same genus plants thereof and linden (*Tilia cordata Mill*) and the same genus plants thereof or a processed material obtained therefrom may also be employed as an active ingredient.

As the parts of the plants, an above-ground part, a subterranean part, a leaf, a bark, a xylem, a root, a florescence, a fruit, a pericarp, a seed, etc. can be mentioned. Specifically, a pericarp of angelica, a florescence of linden and the like are mentioned.

Processed material obtained from the above-mentioned parts of the plants include dried matters, extractants, steam-distilled matters, pressed matters, pulverized matters, ground matters, partially refined matters and refined matters. These may be obtained from the plants in the conventional procedure used for the preparation of vegetable drugs. Specifically, a pericarp of angelica is extracted with a solvent such as water, ether, ethyl acetate, acetonitrile, acetone, methanol, ethanol, dichloromethane, chloroform, toluene, benzene, hexane, heptane and 1,3-butylene glycol or a mixed solvent thereof at ordinary temperature or elevated temperature. Moreover, florescences of linden is extracted with a solvent such as water, ether, ethyl acetate, an acetonitrile, acetone, methanol, ethanol, dichloromethane, chloroform, toluene, benzene, and hexane, heptane and 1,3-butylene glycol, or a mixed solvent thereof. The resulting extractants themselves may also be used as an active ingredient. Furthermore, partially refined or refined matters obtained by fractioning such extractants by column chromatography using silica gel, alumina, cellulose powder or the like, high performance liquid chromatography, thin-layer chromatography and the like may also be used as an active ingredient.

In the above-mentioned accumulation inhibitor (III) of the present invention, the above-mentioned active ingredients are formulated with a pharmacologically acceptable carrier.

The present invention also provides a method for inhibiting a collagen accumulation [the accumulation inhibiting method (IV) of the present invention] comprising a step for administering a positive regulatory factor of a collagen accumulation-inhibiting pathway which is dependent on the protein of the present invention to a cell having a type-I collagen gene under a condition allowing a positive regulatory factor of a collagen accumulation-promoting pathway to be present outside of said cell.

The "cell having a type-I collagen gene" used herein is the same as explained in said accumulation inhibiting method (III) of the present invention. The "condition allowing a positive regulatory factor of a collagen accumulation-promoting pathway to be present outside of said cell" is the same as explained in said accumulation inhibiting method (I) of the present invention.

EXAMPLES

The present invention is further described in the following Examples, which are not intended to restrict the present invention.

Example 1

Preparation of DNA of Invention as Active Ingredient of Collagen Accumulation Inhibitor of Invention (1) Preparation of Vector Expressing Exogenous Gene Encoding DNA-binding Protein of Invention A human fetal dermal fibroblast (Clontech, Catalog No.CC-2509) was incubated in a population of $1 \times 10^7$ cells overnight at 37° C. under 5% $CO_2$ atmosphere. The cell thus incubated was washed twice with a PBS and suspended in 1 ml of TRIZOL reagent (Gibco BRL, Catalog No.15596-018). The cell suspension thus obtained was allowed to stand at room temperature for 5 minutes, combined with 0.2 ml of chloroform, stirred for 15 seconds, and centrifuged at 4° C. at 15,000 rpm for 15 minutes. The aqueous layer was recovered, combined with 0.5 ml of isopropanol, allowed to stand at room temperature for 5 minutes, and centrifuged at 4° C. at 15,000 rpm for 10 minutes. The pellet thus recovered was combined with 1 ml of 70% ethanol, and then centrifuged at 4° C. at 12,000 rpm for 5 minutes. The pellet thus recovered was air-dried, and dissolved in 20 µl of TE solution [composition: 10 mM Tris HCl (pH8.0), 1 mM sodium ethylene diamine tetraacetate (hereinafter abbreviated as EDTA) (pH8.0)] (the solution thus obtained was hereinafter referred to as the total RNA solution). Then THERMPSCRIPT RT-PCR System (Gibco BRL, Catalog No.11146-024) was employed to perform a reverse transcription as described below. Thus, 2 µl of the total RNA solution, 1 µl of Oligo $(dT)_{20}$ and 7 µl of DEPC-treated water were mixed and immediately after keeping at 65° C. for 5 minutes the mixture was cooled on ice. Then the mixture was combined with 4 µl of 5×cDNA synthesis Buffer, 1 µl of RNaseOUT, 1 µl of DTT, 1 µl of DEPC-treated water, 2 µl of 10 mM dNTP Mix and 1 µl of THERMOSCRIPT RT, and the mixture was kept at 55° C. for 1 hour followed by 85° C. for 5 minutes. Then the mixture was combined with 1 µl of RNase H, and kept at 37° C. for 20 minutes. 1 µl of the mixture thus obtained, 1 µl of the oligonucleotide consisting of the nucleotide sequence represented by SEQ ID No:5 (10 pmol/µl), 1 µl of the oligonucleotide consisting of the nucleotide sequence represented by SEQ ID No:.6 (10 pmol/µl), 29 µl of distilled water, 5 µl of the buffer included in TaKaRa LA Taq (TAKARA, Catalog No.RR002A), 5 µl of a $Mg^{2+}$ solution, 5 µl of dNTP mixture and 0.5 µl of LA Taq were mixed and then the mixture thus obtained was kept at 94° C. for 5 minutes. Then the mixture was subjected to 35 cycles, each cycle involving the incubations at 94° C for 1 minute, 60° C. for 1 minute and then 72° C. for 2 minutes, and further kept at 72° C. for 7 minutes. The mixture after these incubations was subjected to an electrophoresis on 1% Agarose L (Nippon Gene, Catalog No.317-01182) gel. An about 1 kb DNA-containing gel portion was cut out, and kept at 65° C. for 5 minutes. The gel solution thus obtained was combined with an equal volume of phenol and mixed, and then centrifuged at 15,000 rpm for 3 minutes. The supernatant thus recovered was combined with an equal volume of chloroform and mixed, and then centrifuged at 15,000 rpm for 3 minutes to recover a supernatant again (hereinafter this procedure is referred to as a phenol-chloroform treatment). The supernatant thus recovered was combined with 1/9-volume 3M sodium acetate and 2-volume ethanol, allowed to stand at −80° C. for 30 minutes, and then centrifuged at 15,000 rpm for 15 minutes to obtain a pellet. The pellet thus recovered was combined with 1 ml of a cold 80% ethanol, centrifuged at 15,000 rpm for 5 minutes, and the pellet was recovered again. The pellet recovered was combined with 40 µl of distilled water, 5 µl of 10×H Buffer (Takara), 2.5 µl of BamHI (15 U/µl, Takara, Catalog No. 1060A) and 2.5 µl of XhoI (15 U/µl, Takara, Catalog No. 1093A), and the mixture was kept at 37° C. for 3 hours. This mixture was then subjected to a 1% agarose gel electrophoresis. An about 1 kb DNA-containing gel portion was cut out, and subjected to a phenol-chloroform treatment as described above followed by an ethanol precipitation, whereby recovering a DNA. The DNA thus recovered was dissolved in 20 µl of TE solution to obtain a solution of an intended DNA (exogenous gene encoding the DNA-binding protein of the present invention: hereinafter sometimes referred to as the DNA of the present invention).

A vector DNA was prepared as described below. 5 µg of vector pET-28a (+) (Novagen, Catalog No.69864-3), 5 µl of 10×K Buffer (Takara), 2.5 µl of BamHI and 2.5 µl of XhoI were mixed and combined further with distilled water to make the total volume 50 µl. The mixture thus obtained was kept at 37° C. for 3 hours and then subjected to a 1% agarose gel electrophoresis. A vector DNA-containing gel portion was cut out, and subjected to a phenol-chloroform treatment as described above followed by an ethanol precipitation, whereby recovering a vector DNA. The pellet thus recovered was combined with 44 µl of distilled water, 5 µl of alkaline phosphatase buffer and 1 µl of alkaline phosphatase (Takara, Catalog No.2120A), kept at 65° C. for 30 minutes, combined with 1 µl of 1% sodium dodecyl sulfate, 2.5 µl of 0.2 M EDTA and 1 µl of 1% proteinase K (Wako, Catalog No.), and then kept at 55° C. for 30 minutes (hereinafter this procedure is referred to as a BAP treatment). Then this mixture was combined with 450 µl of distilled water, subjected to a phenol-chloroform treatment followed by an ethanol precipitation, whereby recovering a DNA. The DNA thus recovered was dissolved in 20 µl of TE solution to obtain a vector DNA (hereinafter sometimes referred to as the vector DNA of the present invention).

Then 5 µl of the solution of the DNA of the present invention, 1 µl of the solution of the vector DNA of the present invention and 6 µl of the enzyme solution of DNA Ligation kit Ver 2 (Takara, Catalog No.6022) were mixed, and the resultant mixture was kept at 16° C. over one whole day and night. This mixture was combined with 100 µl of E. coli BL21-GOLD (DE3) (TOYOBO, Catalog No. SC230132) and allowed to stand on ice for 30 minutes, kept at 42° C. for 45 seconds, and the resultant E. coli was inoculated on an LB plate (1% tryptone, 0.5% yeast extract, 1% sodium chloride, 1.5% bactoagar) containing 30 µg/ml of kanamycin sulfate (Gibco, Catalog No.15160-054), which was allowed to stand at 370C over one whole day and night. By isolating a single colony which had emerged, an E. coli containing a vector expressing an exogenous gene encoding the DNA-binding protein of the present invention (hereinafter sometimes referred to as the DNA-binding protein expressing vector containing E. coli ) was obtained. On the other hand, the single colony was incubated in 2 ml of an LB medium (1% tryptone, 0.5% yeast extract, 1% sodium chloride) containing 30 µg/ml of kanamycin sulfate at 37° C. for 12 hours. From a culture fluid thus obtained, a plasmid DNA was prepared using Automatic DNA Isolation System PI-50 (KURABO). Thus a vector expressing an exogenous gene encoding the DNA-binding protein of the present invention was obtained.

(2) Preparation of DNA-binding Protein of Invention

The E. coli containing a vector expressing the DNA-binding protein of the present invention obtained in Example 1(1) was inoculated to 200 ml of an LB medium containing 30 µg/ml of kanamycin sulfate, and incubated at 37° C. until $OD_{600}$ was raised to 0.4 to 0.6. The culture fluid thus obtained was supplemented with isopropyl-β-D-thiogalactopyranoside (hereinafter abbreviated as IPTG) at the final concentration of 0.5 mM, and then incubated at 37° C. for another 3 hours. The resultant culture fluid was centrifuged (5,000 rpm, 10 minutes, 40° C.) to recover a pellet (bacterial cell), which was then combined with 10 ml of Binding buffer [5 mM imidazole, 0.5 M NaCl, 5 mM $MgCl_2$, 10% glycerol, 20 mM Tris-HCl (pH7.5)] to form a cell suspension, which was treated ultrasonically until its viscosity was lost. The ultrasonically-treated cell suspension thus obtained was centrifuged (12,000 rpm, 30 minutes, 4° C.) to obtain a supernatant. Then the supernatant obtained was loaded onto a nickel-NTA-agarose column (QUIAGEN). Subsequently, the column was eluted with 2-volume Binding buffer followed by 5-volume Washing buffer [20 mM imidazole, 0.5 M NaCl, 5 mM $MgCl_2$, 10% glycerol, 20 mM Tris-HCl (pH7.5)], further followed by Elute buffer [200 mM imidazole, 0.5 M NaCl, 5 mM $MgCl_2$, 10% glycerol, 20 mM Tris-HCl (pH7.5)], whereby eluting an intended protein out of the column and recovering the effluent. An aliquot of the effluent thus recovered was subjected to a sodium dodecyl sulfate (hereinafter abbreviated as SDS) −13% polyacrylamide gel electrophoresis. As a result of staining the gel with silver after the electrophoresis, a single band at the position in the gel corresponding to the DNA-binding protein of the present invention was observed.

A substantial amount of the effluent was dialyzed at 4° C. against the solution containing 10 mM HEPES-KOH (pH7.9), 40 mM KCl, 0.4 mM EDTA, 4% glycerol, 0.5 mM dithiothreitol (DTT), 0.5 mM phenylmethylsulfonyl fluoride (PMSF), 2 µg/ml of leupeptin, 2 µg/ml of pepstatin A] and then concentrated using *CENTRICON* 30 (Amicon) to obtain the DNA-binding protein of the present invention.

Example 2

Ability of Inhibiting Transcription of Type-I Collagen Gene Possessed by DNA-binding Protein of Invention (1) Preparation of (a) DNA Containing Nucleotide Sequence Required for Initiating Transcription and having Type-I Collagen Gene Expression Regulatory Region (Binding Probe) and (b) DNA Containing Nucleotide Sequence Required for Initiating Transcription and having Nucleotide Sequence having No Ability of Binding to DNA-binding Protein of Invention (Non-binding Probe)

An oligonucleotide consisting of the nucleotide sequence represented by SEQ ID No:.3 was mixed with an oligonucleotide consisting of the nucleotide sequence complementary with its nucleotide sequence, and this oligonucleotide mixture was boiled for 5 minutes and then allowed to stand at room temperature. Then this oligonucleotide mixture in an amount corresponding to 10 pmol DNA, 2 µl of a T4 kinase buffer, 1 µl of T4 kinase and 6 µl of γ-$^{32}$P-ATP(>3000 Ci/mmol, DAIICHI KAGAKU YAKUHIN, Catalog No.NEG-502A) were mixed with distilled water to make the total volume 20 µl, which was then kept at 37° C. for 1 hour. This mixture was loaded onto Quick Spin Column G-25 (Boehringer, Catalog No.1273949). This column was centrifuged (2,500 rpm, 5 minutes), and the effluent was recovered. The effluent thus recovered was subjected to a 10% polyacrylamide gel electrophoresis to recover a gel portion containing a $^{32}$P-labelled double-stranded DNA. the gel portion thus recovered was combined with distilled water, kept at 37° C. over one whole day and night, and extracted to obtain the $^{32}$P-labelled DNA (hereinafter referred to as the binding probe). Thus the binding probe was prepared.

On the other hand, an oligonucleotide consisting of the nucleotide sequence (represented by SEQ ID No:.7) resulting from the replacement of the bases represented by Base No.5 and Base No.6 in the nucleotide sequence represented by SEQ ID No:.3 was mixed with an oligonucleotide consisting of the nucleotide sequence complementary to its nucleotide sequence, and this oligonucleotide mixture was subjected to the procedure similar to that for preparing the binding probe described above, and extracted to obtain a $^{32}$P-labelled DNA (hereinafter referred to as a non-binding probe). Thus the non-binding probe was prepared.

(2) Gel Shift Assay 200 ng of the DNA-binding protein of the present invention prepared in Example 1 (2) and 1 µg of Poly dI-dC were combined with either one of the two probes prepared in Section (1) described above (each 50,000 cpm) and the mixture was allowed to stand on ice for 30 minutes. Then the entire amount of each mixture was subjected to a polyacrylamide gel electrophoresis (150 V, 4° C., 150 minutes). After completion of the electrophoresis, the gel was immersed in a 3:1:6 (v/v/v) mixture of methanol, acetic acid and water to fix. The fixed gel was dried using a gel drier, and exposed to an X-ray film. In a case in which a binding probe was used, a radioactive signal was detected in the position of the band of the DNA-binding protein of the present invention On the other hand, in a case in which a non-binding probe was used, no radioactive signal in the position of the band of the DNA-binding protein of the present invention was exhibited.

In accodance with the result thus confirmed, the following design of primer (the oligonucleotides of SEQ ID Nos:10 and 11 were utilized for preparation of the follwing binding reporter vector and the oligonucleotides of SEQ ID Nos:12 and 11 were utilized for preparation of the follwing non-binding reporter vector.) was conducted.

(3) Preparation of Vector having Reporter Gene

A normal human fetal dermal fibroblast is washed with a PBS and suspended in 1 ml of TRIZOL reagent. After allowing the resultant cell suspension to stand at room temperature for 5 minutes, the cell suspension is combined with 0.2 ml of chloroform and shaken for 15 seconds. After allowing to stand at room temperature further for 3 minutes, the mixture is centrifuged (15,000 rpm, 4° C., 15 minutes). The intermediate layer and the organic layer are recovered, combined with 0.3 ml of ethanol, allowed to stand at room temperature for 3 minutes and then centrifuged (3,000 rpm, 4° C., 5 minutes). The pellet recovered is combined with 1 ml of 0.1 M sodium citrate, allowed to stand at room temperature for 30 minutes, and centrifuged (3,000 rpm, 4° C., 5 minutes) to recover a pellet. This procedure is repeated once more. The pellet thus obtained is combined with 2 ml of 75% ethanol, allowed to stand at room temperature for 20 minutes, and centrifuged (3,000 rpm, 4° C., 5 minutes). The pellet is dried in vacuum for 5 minutes and then dissolved in an ultrapure water.

The solution thus obtained, an oligonucleotide consisting of the nucleotide sequence represented by SEQ ID No:.8 and an oligonucleotide consisting of the nucleotide sequence represented by SEQ ID No:.9 are employed to perform a PCR. The PCR solution is kept at 94° C. for 5 minutes, subjected to 30 cycles, each cycle involving the incubations at 94° C. for 1 minute, 55° C. for 2 minutes and then 72° C. for 3 minutes. After completion of the PCR, the PCR solution was subjected to a 1% agarose gel electrophoresis to recover an about 2.5 kb DNA. The DNA thus recovered is subjected to a phenol-chloroform treatment followed by an ethanol precipitation, whereby obtaining a DNA. The DNA thus recovered is dissolved again in an ultrapure water, combined with 2.5 µl of BamHl and 2.5 µl of HindIII (Nippon Gene, Catalog No.311-01163), kept at 37° C. for 3 hour, and subjected to a 1% agarose gel electrophoresis to recover an about 2.5 kb DNA. The DNA thus recovered was subjected to an ethanol precipitation to obtain an intended DNA (hereinafter referred to as a promoter DNA).

On the other hand, vector p8-CAT having a nucleotide sequence encoding a chloramphenicol acetyl transferase (hereinafter abbreviated as CAT) [J. Biol. Chem., 265, 13351-13356 (1990)] was digested with BamHI and HindIII and then subjected to an agarose gel electrophoresis as described above to recover an about 5 kb DNA. The DNA thus recovered was subjected to an ethanol precipitation to obtain a DNA. This DNA was subjected to a BAP treatment, followed by a phenol-chloroform treatment, followed by an ethanol precipitation, whereby recovering a DNA (hereinafter referred to as a CAT vector DNA). Then the promoter DNA described above and the CAT vector DNA are mixed, and the mixture is supplemented with a DNA Ligation kit Ver 2 enzyme solution, and kept at 16° C. over one whole day and night. This mixture is combined with E. coli 5Hdα (TOYOBO, Catalog No. DNA-903), allowed to stand on ice for 30 minutes and then kept at 42° C. for 45 seconds, and the resultant E. coli is inoculated onto an LB plate containing 50 µg/ml sodium ampicillin (NACALAI, Catalog No.027-39), and allowed to stand at 37° C. over one whole day and night. A single colony which had emerged is inoculated in 2 ml of an LB medium containing 50 µg/ml sodium ampicillin, incubated at 37° C. for 12 hours, and the resultant culture fluid was subjected to Automatic DNA Isolation System PI-50 (KURABO) to obtain a plasmid DNA. The nucleotide sequence of the plasmid DNA thus obtained is analyzed using a DNA sequencer to ensure that the intended nucleotide sequence is possessed. 100 ng of this plasmid DNA is employed as a template, and combined with each 10 pmol of an oligonucleotide consisting of the nucleotide sequence represented by SEQ ID No:.10 and an oligonucleotide consisting of the nucleotide sequence represented by SEQ ID No:.11 to perform a PCR. The PCR solution is kept at 94° C. for 5 minutes, subjected to 30 cycles, each cycle involving the incubations at 94° C. for 1 minute, 55° C. for 1 minute and then 72° C. for 1 minute. After completion of the PCR, the PCR solution is subjected to a 1% agarose gel electrophoresis to recover an about 0.22 kb DNA. The DNA thus recovered is digested with BamHI and HindIII and subjected to a 1% agarose gel electrophoresis to recover an about 0.22 kb DNA. The DNA thus recovered is ligated with a CAT vector DNA and then the ligated DNA is transduced into an E. coli 5Hdα. The transformant thus obtained is used to prepare a plasmid DNA to obtain a plasmid in which a nucleotide sequence encoding the CAT is ligated downstream of the nucleotide sequence from the −161 to +57 positions (transcription starting point is +1) in the promoter region of the human type-I collagen α2 strand gene is obtained (hereinafter referred to as the binding reporter vector). The nucleotide sequence of this plasmid is identified by analyzing using an automatic DNA sequencer.

Then the binding reporter vector is digested with BamHI and HindIII, and the digestion product is subjected to a 3% agarose gel electrophoresis to obtain a DNA having a nucleotide sequence encoding the CAT.

On the other hand, each 10 pmol of an oligonucleotide consisting of the nucleotide sequence represented by SEQ ID No:.12 and an oligonucleotide consisting of the nucleotide sequence represented by SEQ ID No:.11 were added and a PCR was performed using 100 ng of the binding reporter vector as a template. The PCR solution was kept at 94° C. for 5 minutes, subjected to 30 cycles, each cycle involving the incubations at 94° C. for 1 minute, 55° C. for 1 minute and then 72° C. for 1 minute. After completion of the PCR, the PCR solution was subjected to a 1% agarose gel electrophoresis to recover an about 0.22 kb DNA. The DNA thus recovered was digested with 2.5 µl of BamHI and 2.5 µl of HindIII and subjected to a 3% agarose gel electrophoresis to recover an about 0.22 kb DNA. The DNA thus recovered was ligated with a CAT vector DNA and then the ligated DNA was transduced into an E. coli 5Hdα. The resultant transformant was used to prepare a plasmid DNA to obtain a plasmid in which the cytosines in the positions of −160 and −159 (transcription starting point is +1) in the expression regulatory region of the human type-I collagen α2 strand gene contained in the binding reporter vector (COL1A2) were replaced with guanines (hereinafter referred to as the non-binding reporter vector). The nucleotide sequence of this plasmid was identified using an automatic DNA sequencer (ABI PRISM, 377 DNA Sequencer).

(4) Reporter Gene Expression Assay

Similarly to Example 1 (1), a DNA encoding the DNA-binding protein of the present invention was cloned between the HindIII cleavage site and the XbaI cleavage site of the expression vector pRc/RSV (Invitrogen, Catalog No. 28-0051) and the resultant vector was designated as YB-1/RSV (a vector expressing the DNA-binding protein of the present invention).

A human glioblastoma cell AG-373 [American Type Culture Collection (ATCC), Catalog No.HTB-17] was inoculated in a population of 1×10$^6$ cells in a 60-mm dish (BECTON DICKINSON, Catalog No.3002) and incubated in an MEM medium (GIBCO BRL, Catalog No.11095-072) supplemented with a 10% inactivated fetal bovine serum (hereinafter abbreviated as FBS, Gibco, Catalog No.21140-079), 8.9 mg/l L-alanine, 15 mg/l L-asparagine.H$_2$O, 13.3 mg/l L-aspartic acid, 14.7 mg/l L-glutamic acid, 7.5 mg/l glycine, 11.5 mg/l L-proline and 10.5 mg/l L-serine (hereinafter abbreviated as MEM(+)) at 37° C. in the presence of 5% CO$_2$ overnight, and then the medium was replaced with an MEM medium containing no FBS (hereinafter abbreviated as MEM(−)).

To 100 µl of MEM(−), either of 2 µg of the binding reporter vector or 2 µg of the non-binding reporter vector and either 4 µg of YB-1/RSV or 4 µg of pRc/RSV were added and the mixture was allowed to stand at room temperature for 40 minutes (Solution 1). To 100 µl of MEM(−), 20 µl of Lipofectine (Gibco, Catalog No.18292-011) was added and the mixture was allowed to stand at room temperature for 40 minutes (Solution 2). Then Solution 1 and Solution 2 were mixed and allowed to stand at room temperature for 10 minutes, and then combined with 2 ml of MEM(−) and mixed thoroughly. This mixture was added to the glioblastoma cell described above, which was then incubated at 37° C. under 5% CO$_2$ atmosphere for 6 hours. Subsequently, the culture supernatant was removed from the dish and the cell was washed twice with MEM(−), combined with 4 ml of MEM (+), and then incubated at 37° C. under 5% CO$_2$ atmosphere further for 40 hours.

The cultured cell was washed twice with a PBS, combined with 200 µl of a cell lysis reagent (TOYO INK, Catalog No.PD10) and scraped from the wall of the vessel using a cell scraper (Nalgen, Catalog No.179693). The cell thus scraped was suspended in a cell suspending agent, and the suspension thus formed was centrifuged (15,000 rpm, 4° C., 5 minutes) to recover a supernatant. The supernatant thus obtained (20 µg as protein) was combined with 10 µl of 10 mM acetyl-CoA (Sigma, Catalog No.A2056) and 2 µl of D-threo-[dichloroacetyl-1-$^{14}$C]chloramphenicol (Amersham, Catalog No.CFA754), and the mixture was kept at 37° C. for 5 hours. Then, this mixture was combined with 100 µl of ethyl acetate, mixed and centrifuged (15,000 rpm, 4° C., 5 minutes) to recover an upper layer. The upper layer thus obtained was evaporated into dryness under a nitrogen flow, and the residue was dissolved in 30 µl of ethyl acetate. The entire amount of this solution was developed in a thin layer chromatography on a silica gel (thin layer plate: Silica gel TLC plate, 20×20 cm, MERCK, Catalog No.1.05715, Solvent system: 95:5 (v/v) mixture of chloroform and methanol). The radioactivity of the thin layer plate was quantified using a BIO-IMAGING analyzer BAStation (FUJI FILM). The CAT activity was calculated in accordance with the following equation. CAT Activity (%)=(Radioactivity of acetylchloramphenicol)/(total radioactivity) The results are shown in Table 1. Thus, in a case of the cell into which the YB-1/RSV which was the vector expressing the DNA-binding protein of the present invention and the binding reporter vector had been transduced, a reduced CAT activity was exhibited when comparing with the cell into which the pRc/RSV which was an expression vector as a control (said vector which did not express the DNA-binding protein of the present invention) and the binding reporter vector had been transduced. On the other hand, no such reduction in the activity was observed in any of the cell into which the vector expressing the DNA-binding protein of the present invention and the non-binding reporter vector had been transduced when comparing with the cell into which the expression vector as a control (said vector which did not express the DNA-binding protein of the present invention) and the non-binding reporter vector had been transduced.

TABLE 1

| Vector transduced into cell | | | | |
|---|---|---|---|---|
| Expression vector | Expression of DNA-binding protein of invention | Reporter vector | Relative CAT activity | Remarks |
| pRc/RSV | Absent | Binding reporter vector | 1.0 | |
| YB-1/RSV | Present | Binding reporter vector | 0.6 | Vector expressing DNA-binding protein of invention |

TABLE 1-continued

Vector transduced into cell

| Expression vector | Expression of DNA-binding protein of invention | Reporter vector | Relative CAT activity | Remarks |
|---|---|---|---|---|
| pRc/RSV | Absent | Non-binding reporter vector | 1.1 | |
| YB-1/RSV | Present | Non-binding reporter vector | 1.0 | Vector expressing DNA-binding protein of invention |

*A relative CAT activity is a CAT activity in each case based on the CAT activity, as being regarded to be 1.0, of a cell into which the expression vector pRc/RSV and the binding reporter vector has been transduced.

Example 3

Method for Inhibiting Collagen Accumulation by Transducing Exogenous Gene Encoding DNA-Binding Protein of Invention (1) Preparation of Probe 1 µg of the total RNA of a normal human fetal dermal fibroblast and Oligo (dT)$_{20}$ were employed to perform a reverse transcription reaction similarly to Example 1(1). 1 µl of an resultant cDNA solution and each 1 µl of the oligonucleotide consisting of the nucleotide sequence represented by SEQ ID No:.13 (10 pmol/µl) and an oligonucleotide consisting of the nucleotide sequence represented by SEQ ID No:.14 (10 pmol/µl) were employed to perform a PCR similarly to Example 1(1). The PCR solution was subjected to an agarose gel electrophoresis to recover an about 2 kb DNA. The DNA thus recovered was dissolved in 10 µl of a TE solution to obtain an intended DNA solution. 9 µl of the DNA solution thus obtained, 1 µl of a pGEM T-easy vector solution (Promega, Catalog No.A1360) and 10 µl of the enzyme solution of DNA Ligation kit Ver 2 were mixed to effect a ligation. The ligated DNA thus obtained was transduced into an E. coli 5Hdα. The transformant thus obtained was inoculated onto an LB plate containing sodium ampicillin and incubated until a colony was formed. A single colony which had emerged was recovered and incubated again, and then from this transformant a plasmid containing a nucleotide sequence from the 2021st to 4051st bases in the coding region of a human type-I collagen α2 strand was isolated. On the other hand, each 1 µl of an oligonucleotide consisting of the nucleotide sequence represented by SEQ ID No:21 (10 pmol/µl) and an oligonucleotide consisting of the nucleotide sequence represented by SEQ ID No:.22 (10 pmol/µl) were employed instead of the two oligonucleotides described above and subjected to the procedure similar to that described above, whereby isolating a plasmid containing a nucleotide sequence from the 2342nd to 3735th bases in the coding region of a human type-I collagen α1 strand.

Each plasmid thus isolated was digested with XhoI and Sacd and subjected to an agarose gel electrophoresis, whereby recovering about 1.0 kb and about 1.3 kb DNAs, respectively. Each of the DNAs thus recovered was dissolved in a TE solution at about 10 ng/µl to obtain an intended DNA solution. 1 µl of the DNA solution thus obtained was combined with 44 µl of a TE solution and the mixture was kept at 95° C. for 5 minutes, and then place on ice. This mixture was then added to a 1 tube of Random Prime Labelling System (Rediprime II, Amersham Pharmacia, Catalog No.RPN1633), to which 5 µl of [α-$^{32}$P]dCTP (Amersham Pharmacia, Catalog NO.RPNAA0005) was added and mixed. This mixture was kept at 37° C. for 1 hour, and loaded onto a G-50 column (Amersham Pharmacia, Catalog No.27-5335-01). This column was centrifuged at 2,000 g for 2 minutes, and then the effluent was recovered. The effluent thus recovered was kept at 95° C. for 5 minutes, and then placed on ice. The DNA thus prepared was employed as a probe for a northern blotting.

(2) Determination of Type-I Collagen Gene Transcription Quantity (mRNA Quantity)

A normal human fetal dermal fibroblast was inoculated in a population of 5×10$^7$ cells in a 100-mm dish (BECTON DICKINSON, Catalog No.3003) and incubated in D-MEM (+) overnight at 37° C. under 5% CO$_2$ atmosphere. On the following day, the medium was replaced with D-MEM(−).

300 µl of D-MEM(−) was combined with 150 ng of YB-1/RSV or pRc/RSV and the mixture was allowed to stand at room temperature for 45 minutes (Solution 1). On the other hand, 300 µl of D-MEM(−) was combined with 20 µl of Lipofectine and the mixture was allowed to stand at room temperature for 40 minutes (Solution 2). Then, Solution 1 and Solution 2 were mixed and the resultant mixture was allowed to stand at room temperature for 10 minutes and combined with 5.4 ml of D-MEM(−). The mixture thus obtained was supplemented with the human fetal dermal fibroblast described above. This mixture (containing the cell) was incubated at 37° C. under 5% CO$_2$ atmosphere for 6 hours, and then the dish was made free of the supernatant and washed twice with D-MEM(−). Then the dish received 10 ml of D-MEM (0.1%) and incubated at 37° C. under 5% CO$_2$ atmosphere for 1 hour, and then the cell was supplemented with 10 µl of a 5 µg/ml aqueous solution of TGFβ which was a positive regulatory factor of the collagen accumulation promoting pathway (TGFβ level in medium: 5 ng/ml), and then incubated at 37° C. under 5% CO$_2$ atmosphere further for 40 hours. In a case of TGFβ-free, 10 µl of distilled water was used instead of TGFβ. The cell thus incubated was washed twice with a PBS, and used to prepare a total RNA similarly to Example 1 (1). 10 µg of the total RNA, 10 µl of formamide (NACALAITESQUE, Catalog NO.163-45), 4 µl of formalin (WAKO, Catalog No.064-00406), 3 µl of 10×MOPS [41.854 g of 3-(N-morpholino)propanesulfonic acid (NACALAITESQUE, Catalog No.234-38), 6.804 g of sodium acetate and 3.772 g of EDTA were dissolved in distilled water with adjusting at pH7.0 and making the entire volume 1 L] were mixed, and, immediately after keeping at 65° C. for 10 minutes, the mixture was placed on ice. The mixture obtained was subjected to an electrophoresis at 100 V for 60 minutes (gel was prepared by heating 1.5 g of agarose, 15 ml of 10×MOPS and 110 ml of distilled water to dissolve the agarose, followed by adding 25 ml of formalin. Electrophoresis buffer: 1×MOPS). The gel after the electrophoresis was brought into a close contact with a Hybond-N filter (Amersham Pharmacia, Catalog No.RPN303N) and allowed to stand overnight under pressure in 20×SSC (175.32 g of sodium chloride and 88.22 g of sodium citrate were dissolved in distilled water to make 1 L whereby transferring an RNA onto the filter. The filter onto which the RNA had been transferred was kept at 80° C. for 2 hours, and then the filter was kept at 42° C. for 5 hours in 40 ml of a hybridization buffer (25 ml of formamide, 12.5 ml of 20×SSC, 5 ml of 0.5 M sodium phosphate (pH6.5), 0.2 ml of salmon sperm DNA solution (Gibco BRL, Catalog No.15632-011), 4 ml of 5× Denhart solution (WAKO, Catalog No.043-21871), 3.3 ml of distilled water). Subsequently, the hybridization buffer was removed, and 10 ml of a fresh hybridization buffer was loaded onto the filter, to which the probe for the northern blotting prepared in Section (1) described above (having the nucleotide sequence from the 2631st to the 3654th bases in the coding region of the human type-I collagen α2 strand) was further added at $10^8$ cpm/ml, and kept at 42° C. overnight. Then the probe solution was removed, and 100 ml of 2×SSC supplemented with 0.1% SDS was added to the filter, which was kept at room temperature for 10 minutes. This procedure was repeated two more times. To the filter thus obtained, 100 ml of 0.1×SSC supplemented with 0.1% SDS was added, and the incubation at 50° C. for 20 minutes was repeated three times and the filter was then air-dried. The radioactivity of the air-dried filter was determined using BAStation. The filter after the hybridization described above was then kept in 0.1×SSC for 10 minutes and then at 42° C. for 5 hours in the hybridization buffer. To this filter, the probe for the northern blotting (having the nucleotide sequence from the 2381st to the 3685th bases in the coding region of the human type-I collagen α1 strand) was added and the hybridization was performed as described above.

On the other hand, 10 μg of the total RNA was subjected to an electrophoresis on the gel described above which contained 0.5 μg/ml of ethidium bromide (Gibco BRL, Catalog No.15582-018) and the fluorescent intensity of 28S ribosome RNA was quantified using Luminescent Image Analyzer LAS-1000 plus (FUJI FILM) and Image Gauge Ver 3.12 (FUJI FILM). The quantity of the mRNA of each gene relative to the 28S ribosome RNA was calculated in accordance with the following equation. Quantity of mRNA=Radioactivity of band of about 5 kb/fluorescent intensity of 28S ribosome RNA The results are shown in Table 2. Thus, the collagen accumulation inhibition as a result of the transduction of the exogenous gene encoding the DNA-binding protein of the present invention was identified at an mRNA level. In addition, such effect was identified satisfactorily also under the condition allowing a positive regulatory factor of the collagen accumulation promoting pathway to be present outside of a cell.

TABLE 2

| Expression vector | Presence or absence of expression of DNA-biding protein of invention | Presence or absence of positive regulatory factor (TGFβ) of collagen accumulation promoting pathway | Relative transcription level of type-I collagen gene (mRNA level) α1 strand | α2 strand | Remarks |
|---|---|---|---|---|---|
| pRc/RSV | Absent | Absent | 1.0 | 1.0 | |
| YB-1/RSV | Present | Absent | 0.9 | 0.8 | Expression vector of DNA-binding protein of invention |
| pRc/RSV | Absent | Present | 7.5 | 2.7 | |
| YB-1/RSV | Present | Present | 3.2 | 1.5 | Expression vector of DNA-binding protein of invention |

*A relative transcription level of type-I collagen (α1 strand or α2 strand) gene (mRNA level) is a type-I collagen gene transcription level (mRNA level) in each case based on the type-I collagen gene transcription level (mRNA level) in a case of TGFβ-free of pRc/RSV-transduced cell as being regarded to be 1.0.

Example 4

Method for Inhibiting Collagen Accumulation by Administration of DNA-binding Protein of the Present Invention (1) Preparation of Cell Extract Similarly to Example 3 (2), a YB-1/RSV which was a vector expressing the DNA-binding protein of the present invention or a pRc/RSV which was a vector expressing no DNA-binding protein of the present invention was transduced into a normal human fetal dermal fibroblast, and the transformant was combined with TGFβ which was a positive regulatory factor of a collagen accumulation-promoting pathway and then incubated at 37° C. under 5% $CO_2$ atmosphere for 40 hours. In a case of TGFβ-free, an equal volume of distilled water was added instead of TGFβ. A cell thus incubated was washed twice with a PBS, and the dish on which the incubated cell was present received 0.5 ml of a RIPA buffer (50 mM Tris HCl (pH7.5), 150 mM sodium chloride, 1% NP-40, 0.5% deoxycholic acid, 0.1% SDS, 1 mM PMSF, 2.5 mM EDTA, 1 mM $Na_3VO_4$, 20 μg/ml aprotinin, 10 μg/ml leupeptin, 50 mM sodium fluoride) and then the cell was recovered from the dish. A cell suspension thus obtained was passed through a 22 G injection syringe, and then allowed to stand on ice for 1 hour. The cell suspension was then centrifuged at 4° C. and 15,000 rpm for 10 minutes to recover a supernatant (hereinafter referred to as a cell extract). The cell extract was examined for its protein content using a DC protein assay (Bio-Rad, Catalog No.500-0113). Thus, a 96-well microplate received 5 μl of the cell extract, 25 μl of reagent A and 200 μl of reagent B and was then shaken to mix, and the mixture was allowed to stand at room temperature for 15 minutes and examined for its absorbance at 655 nm.

(2) Determination of Type-I Collagen Protein

25 μg of the cell extract was combined with an equal volume of a SDS sample buffer (100 mM Tris-HCl (pH7.5), 20% glycerol, 4% SDS, 2% mercaptoethanol, 0.01% bromophenol blue) and the mixture was kept at 95° C. for 5 minutes. The entire amount of this mixture was subjected to an SDS-13% polyacrylamide gel electrophoresis (40 mA constant current, electrophoresis buffer: 0.25 M Tris, 1.92 M glycine, 1% SDS). After completion of the electrophoresis, the gel was brought into a close contact with a nitrocellulose membrane (Amersham, Catalog No.RPN303E) to transfer (250 mA constant current, transfer buffer: 20% methanol, 0.25 M Tris, 1.92 M glycine, 1% SDS). The membrane thus transferred was immersed in a 5% skimmed milk (WAKO, Catalog No.) and shaken at 4° C. overnight. Then, this membrane was immersed in a PBS containing 0.1% Tween 20 (hereinafter referred to as a PBS-T) and shaken at room temperature for 10 minutes, this procedure being performed twice, and then the membrane was immersed in a 1000-fold diluted rabbit anti-human type-I collagen antibody (Polysciences, Catalog No.23706) and shaken at room temperature for 1 hour. Subsequently, the membrane was immersed in a PBS-T and shaken at room temperature for 15 minutes, this procedure being performed three times, and the membrane was immersed a 5000-fold diluted horse radish peroxidase-labelled goat anti-rabbit IgG antibody (diluted with PBS-T), and shaken at room temperature for 1 hour. The membrane was further immersed in a PBS-T and shaken at room temperature for 15 minutes, this procedure being performed three times, and the color was developed using a Western blot detection kit (Amersham, Catalog No.RPN2106), and then a BIOMAX MR film (Kodak, Catalog No.8912560) was exposed to this color development. The film thus exposed was printed and then the film was digitized (transmitted) via a white light using a LUMINESCENT IMAGE ANALYZER LAS-1000 plus (FUJI FILM) into a digital image, whose blackening degree was quantified using an Image Gauge ver 3.12 (FUJI FILM). From the value obtained, a relative level of the type-I collagen protein was calculated.

The results are shown in Table 3. Thus, the collagen accumulation inhibition as a result of the transduction of the exogenous gene encoding the DNA-binding protein of the present invention was identified at a protein level. In addition, such effect was identified satisfactorily also under the condition allowing a positive regulatory factor of the collagen accumulation promoting pathway to be present outside of a cell.

TABLE 3

| Expression vector | Presence or absence of expression of DNA-biding protein of invention | Presence or absence of positive regulatory factor (TGFβ) of collagen accumulation promoting pathway | Relative amount of type-I collagen protein | Remarks |
|---|---|---|---|---|
| pRc/RSV | Absent | Absent | 1.0 | |
| YB-1/RSV | Present | Absent | 0.8 | Expression vector of DNA-binding protein of invention |
| pRc/RSV | Absent | Present | 2.2 | |
| YB-1/RSV | Present | Present | 1.4 | Expression vector of DNA-binding protein of invention |

*A relative amount of type-I collagen protein is an amount of type-I collagen protein in each case based on the amount of type-I collagen protein in a case of TGFβ-free of pRc/RSV transduced cell as being regarded to be 1.0.

Example 5

Method for Searching for Substance Regulating Type-I Collagen Gene Transcription Regulating Ability: Evaluation of Type-I Collagen Gene Transcription Regulating Ability by Measuring Intracellular Migration Level of DNA-binding Protein of Invention or Index Correlating Therewith (1) Preparation of Vector Expressing Protein having Amino Acid Sequence of DNA-binding Protein of Invention and Amino Acid Sequence of Exogenous Marker Protein (GFP)
100 ng of YB-1/RSV, 10 pmol of an oligonucleotide consisting of the nucleotide sequence represented by SEQ ID NO:.15, 10 pmol of an oligonucleotide consisting of the nucleotide sequence represented by SEQ ID NO:.16, 5 μl of the buffer included in KOD-Dash (TOYOBO, Catalog No.RR002A), 5 μl of $Mg^{2+}$ solution, 5 μl of dNTP mixture, 1 μl of KOD-Dash and distilled water were mixed to prepare 50 μl in total of a PCR solution, which was used to perform a PCR. The condition of the PCR involved an incubation at 94° C. for 2 minutes, followed by 35 cycles, each cycle involving the incubations at 94° C. for 15 seconds, 60° C. for 30 seconds and then 68° C. for 1 minute. After the PCR, the PCR solution was digested with HindIII and PmlI and subjected to an ethanol precipitation to recover a DNA (hereinafter a DNA obtained as a residue is referred to as a YB-1DNA.). On the other hand, pCMX-hGR-GFP (Ogawa, Umezono, J. Histochem. Cytochem. 1999, Vol.31, page 303-308) was digested with HindIII and PmlI, and the digestion product thus obtained was subjected to an agarose gel electrophoresis to separate and recover an about 5 kb DNA containing no hGR. The DNA thus recovered was subjected to a BAP treatment followed by an ethanol precipitation to recover a DNA (hereinafter a DNA obtained as a precipitate is referred to as a GFP vector DNA.). After ligating the YB-1DNA and the GFP vector DNA, the ligated DNA thus obtained was transduced into an E. coli Dh5α. The transformant thus obtained was inoculated onto an LB plate containing ampicillin and incubated until a colony was formed, whereby obtaining an E. coli clone. This E. coli clone was further incubated and a plasmid DNA was prepared by a conventional method from the E. coli thus incubated. The nucleotide sequence of the plasmid DNA thus obtained was analyzed, and a plasmid having a nucleotide sequence in which a GFP amino acid sequence was encoded downstream of the amino acid sequence of the DNA-binding protein of the present invention with its reading flame being continued was selected. The plasmid thus selected was designated as pCMX-YB-1-GFP.
(2) Transduction and Fluorescent Microscope Examination of Expression Vector A human fibroblast was inoculated in a population of $5 \times 10^6$ cells in a 6-well microplate (BECTON DICKINSON, Catalog No.3046) and incubated in D-MEM (+) overnight at 37° C. under 5% $CO_2$ atmosphere.

To 100 μl of D-MEM(−), 1 μg of pCMX-YB-1-GFP and 10 μl of Plus reagent (Gibco BRL, Catalog No.11514-015) were added, and the mixture was allowed to stand at room temperature for 15 minutes (Solution 1). On the other hand, 100 μl of D-MEM(−) was combined with 6 μl of Lipofectamine (Gibco BRL, Catalog No.18324-012), and the mixture was allowed to stand at room temperature for 15 minutes (Solution 2).

Subsequently, Solution 1 and Solution 2 were mixed, and allowed to stand at room temperature for 15 minutes, and then combined with 1 ml of MEM(−) and further with the cell incubated as described above. The mixture (including the cell) was incubated at 37° C. under 5% $CO_2$ atmosphere for 6 hours, and the plate was made free of the supernatant and washed twice with MEM(−). The plate was then combined with 2 ml of MEM(+), incubated at 37° C. under 5% $CO_2$ atmosphere further for 36 hours, brought into contact with a sample of an angelica extract or a linden extract described in Example 9, and then further incubated at 37° C. under 5% $CO_2$ atmosphere for 4 hours. After incubation, the plate was washed with a PBS, and examined by a fluorescent microscope (NIKON, DIAPHOT-TMD) under a FITC filter at a magnification of 100. A negative control employed DMSO (at a final concentration of 0.1%) instead of the sample, while a positive control employed IFN-γ (at a final concentration of 100 U/ml) instead of the sample. A cell which had been brought into contact with the angelica extract sample or the linden extract sample exhibited no cytoplasmic fluorescence similarly to a cell in a case of the positive control, but exhibited a cytoplasmic fluorescence. A cell in a case of the negative control exhibited a cytoplasmic fluorescence but did not exhibit any intranuclear fluorescence.

As a result, it was proven that a substance having a type-I collagen gene transcription regulating ability (an angelica extract sample or a linden extract sample) can be selected for evaluating the type-I collagen gene transcription regulating ability by measuring the quantity of the DNA-binding protein of the present invention migrated into the nucleus of a cell or a parameter having a correlation with said quantity.

Example 6

Method for Searching for Substance Regulating Type-I Collagen Gene Transcription Regulating Ability Utilizing Exogenous Gene Encoding DNA-binding Protein of Invention (1) Preparation of Probe 1 μg of the total RNA of a normal human fetal dermal fibroblast and 10 pmol of the nucleotide sequence represented by SEQ ID No:.13 were employed to perform a reverse transcription reaction similarly to Example 1 (1). 1 μl of the resultant cDNA solution and each 10 p mol of an oligonucleotide represented by SEQ ID No:.13 and an oligonucletide consisting of the nucleotide sequence represented by SEQ ID No:.14 were employed to perform a PCR similarly to Example 1 (1). The PCR solution was kept at 94° C. for 5 minutes, and subjected to 35 cycles, each cycle involving the incubations at 94° C. for 1 minute, 55° C. for 1 minute and then 72° C. for 2.5 minutes. After completion of the PCR, the PCR solution was subjected to an agarose gel electrophoresis to recover an about 2 kb DNA. The DNA thus recovered was dissolved in a TE solution (10 μl) to obtain an intended DNA solution. 9 μl of the DNA solution thus obtained, 1 μl of a pGEM T-easy vector solution (Promega, Catalog No.A1360) and 10 μl of the enzyme solution of DNA Ligation kit Ver 2 were ligated by mixing with each other and the ligated DNA thus obtained was transduced into an E. coli 5Hdα. The transformant thus obtained was inoculated onto an LB plate containing sodium ampicillin and incubated until a colony was formed. A single colony which had emerged was recovered and incubated again, and then from this transformant a plasmid containing a nucleotide sequence from the 2021st to 4051st bases in the coding region of a human type-I collagen α2 strand was isolated. The plasmid thus isolated was digested with EcoRI and XhoI and then subjected to an agarose gel electrophoresis to recover an about 1.4 kb DNA. the DNA thus recovered was dissolved in a TE solution at about 10 ng/μl to obtain an intended DNA solution. 1 μl of the DNA solution thus obtained was combined with 44 μl of a TE solution, and the mixture was kept at 95° C. for 5 minutes and then placed on ice. This mixture was then added to a 1 tube of Random Prime Labelling System (Rediprime II, Amersham Pharmacia, Catalog No.RPN1633), to which 5 μl of [α-$^{32}$P] dCTP (Amersham Pharmacia, Catalog NO.RPNAA0005) was added and mixed. This mixture was kept at 37° C. for 1 hour, and loaded onto a G-50 column (Amersham Pharmacia, Catalog No.27-5335-01). This column was centrifuged at 2,000 g for 2 minutes, and then the effluent was recovered. The effluent thus recovered was kept at 95° C. for 5 minutes, and then placed on ice. The DNA thus prepared was employed as a probe for a northern blotting.

(2) Determination of Type-I Collagen Gene Transcription Quantity (mRNA quantity) in Absence of Positive Regulatory Factor (TGFβ) of Collagen Accumulation Promoting Pathway A normal human fetal dermal fibroblast was inoculated in a population of 5×10$^7$ cells in a 100-mm dish and incubated in D-MEM (+) overnight at 37° C. under 5% CO$_2$ atmosphere. This cell was supplemented with the angelica extract sample prepared in Example 7 (2) at 50 μg lyophilized sample per ml medium and incubated further for 24 hours. In a case of negative control, the angelica extract sample was replaced with DMSO (added at 0.1% in the medium).

In a case of positive control, the angelica extract sample was replaced with INF-γ (added at 100 U/ml in the medium). The cell thus incubated was washed twice with a PBS, and used to prepare a total RNA similarly to Example 1 (1). 10 μg of the total RNA, 10 μl of formamide (NACALAITESQUE, Catalog NO.163-45), 4 μl of formalin (WAKO, Catalog No.064-00406), 3 μl of 10×MOPS [41.854 g of 3-(N-morpholino)propanesulfonic acid (NACALAITESQUE, Catalog No.234-38), 6.804 g of sodium acetate and 3.772 g of EDTA were dissolved in distilled water with adjusting at pH7.0 and making the entire volume 1 L] were mixed, and, immediately after keeping at 65° C. for 10 minutes, the mixture was placed on ice. The mixture obtained was subjected to an electrophoresis at 100 V for 60 minutes (gel was prepared by heating 1.5 g of agarose, 15 ml of 10×MOPS and 110 ml of distilled water to dissolve the agarose, followed by adding 25 ml of formalin. Electrophoresis buffer: 1×MOPS). The gel after the electrophoresis was brought into a close contact with a Hybond-N filter (Amersham Pharmacia, Catalog No.RPN303N) and allowed to stand overnight under pressure in 20×SSC (175.32 g of sodium chloride and 88.22 g of sodium citrate were dissolved in distilled water to make 1 L whereby transferring an RNA onto the filter. The filter onto which the RNA had been transferred was kept at 80° C. for 2 hours, and then the filter was kept at 42° C. for 5 hours in 40 ml of a hybridization buffer (25 ml of formamide, 12.5 ml of 20×SSC, 5 ml of 0.5 M sodium phosphate (pH6.5), 0.2 ml of salmon sperm DNA solution (Gibco BRL, Catalog No.15632-011), 4 ml of 5× Denhart solution (WAKO, Catalog No.043-21871), 3.3 ml of distilled water). Subsequently, the hybridization buffer was removed, and 10 ml of a fresh hybridization buffer was loaded onto the filter, to which the probe for the northern blotting prepared in Section (1) described above was further added at 10$^6$cpm/ml, and kept at 42° C. overnight. Then the probe solution was removed, and 100 ml of 2×SSC supplemented with 0.1% SDS was added to the filter, which was kept at room temperature for 10 minutes. This procedure was repeated two more times. To the filter thus obtained, 100 ml of 0.1×SSC supplemented with 0.1% SDS was added, and the incubation at 50° C. for 20 minutes was repeated three times and the filter was then air-dried. The radioactivity of the air-dried filter was determined using BAStation.

On the other hand, 10 μg of the total RNA was subjected to an electrophoresis on the gel described above which contained 0.5 μg/ml of ethidium bromide (Gibco BRL, Catalog No.15582-018) and the fluorescent intensity of 28S ribosome RNA was quantified using Luminescent Image Analyzer LAS-1000 plus (FUJI FILM) and Image Gauge Ver 3.12 (FUJI FILM). The quantity of the type-I collagen α2 strand mRNA relative to the 28S ribosome RNA was calculated in accordance with the following equation.

Type-I collagen α2 strand mRNA quantity=Radioactivity of band of about 5.8 kb/fluorescent intensity of 28S ribosome RNA The results are shown in Table 4. Thus, it was revalued that the angelica extract sample had a type-I collagen gene transcription regulating ability. Accordingly, it was proven that the method of the present invention can readily select a substance having a type-I collagen gene transcription regulating ability.

TABLE 4

| Test substance | Presence or absence of positive regulatory factor (TGFβ) of collagen accumulation promoting pathway | Relative transcription level of type-I collagen gene (α2 strand mRNA level) |
| --- | --- | --- |
| Negative control | Absent | 1.0 |
| Angelica extract | Absent | 0.5 |

TABLE 4-continued

| Test substance | Presence or absence of positive regulatory factor (TGFβ) of collagen accumulation promoting pathway | Relative transcription level of type-I collagen gene (α2 strand mRNA level) |
|---|---|---|
| sample | | |
| Positive control | Absent | 0.5 |

*A relative transcription level of type-I collagen gene (α2 strand mRNA level) is a type-I collagen gene transcription level (α2 strand mRNA level) in each case based on the type-I collagen gene transcription level (α2 strand mRNA level) in a case of negative control as being regarded to be 1.0.

(3) Determination of Type-I Collagen Gene Transcription Quantity (mRNA quantity) in Presence of Positive Regulatory Factor (TGFβ) of Collagen Accumulation Promoting Pathway A normal human fetal dermal fibroblast was inoculated in a population of $5 \times 10^7$ cells in a 100-mm dish and incubated in D-MEM (+) overnight at 37° C. under 5% $CO_2$ atmosphere. The culture fluid was replaced with D-MEM containing 1% FBS and the incubation was continued for 1 hour, and then the angelica extract sample prepared in Example 7 (2) was added at 50 µg lyophilized sample per ml medium and the incubation was continued further for 1 hour. Subsequently, the culture fluid was supplemented with a human TGFβ (PEPRO TECH, Catalog No.E279) which was a positive regulatory factor of a collagen accumulation-promoting pathway at 10 ng/ml in the medium, and the incubation was continued further for 23 hours. In a case of negative control, the angelica extract sample was replaced with DMSO (added at 0.1% in the medium). In a case of positive control, the angelica extract sample was replaced with INF-γ (added at 100 U/ml in the medium). The cell thus incubated was washed twice with a PBS, and used to prepare a total RNA similarly to Example 1 (1). 10 µg of the total RNA thus obtained was subjected to a northern blotting similarly to Section (2) described above to determine the human type-I collagen α2 strand mRNA quantity based on the 28S ribosome RNA quantity.

The results are shown in Table 5. Thus, it was revealed satisfactorily that the angelica extract sample had a type-I collagen gene transcription regulating ability even under the condition allowing a positive regulatory factor of a collagen accumulation-promoting pathway to be present outside of a cell. Accordingly, it was proven that the method of the present invention can readily select a substance having a type-I collagen gene transcription regulating ability.

TABLE 5

| Test substance | Presence or absence of positive regulatory factor (TGFβ) of collagen accumulation promoting pathway | Relative transcription level of type-I collagen gene (α2 strand mRNA level) |
|---|---|---|
| Negative control | Absent | 1.0 |
| Angelica extract sample | Absent | 0.5 |
| Positive control | Absent | 0.5 |

*A relative transcription level of type-I collagen gene (α2 strand mRNA level) is a type-I collagen gene transcription level (α2 strand mRNA level) in each case based on the type-I collagen gene transcription level (α2 strand mRNA level) in a case of negative control, which employed the positive regulatory factor (TGFβ) of collagen accumulation promoting pathway, as being regarded to be 1.0.

Example 7

Method for Searching for Substance Regulating Type-I Collagen Gene Transcription Regulating Ability Utilizing Type-I Collagen Gene Expression Regulatory Region-binding Reporter Gene (1) Preparation of Reporter Gene which Contains Nucleotide Sequence Required for Initiating Transcription and which is Ligated in a Functional Form to Type-I Collagen Gene Expression Regulatory Region A normal human fetal dermal fibroblast (Clontech, Catalog No.CC-250) was incubated in a population of $1 \times 10^8$ cells overnight at 37° C. under 5% $CO_2$ atmosphere. The cell thus incubated was washed twice with a PBS, combined with 3 ml of a PBS, and scraped from the wall of the vessel using a cell scraper (Nalgen, Catalog No.179693). The cell thus scraped was recovered by a centrifugation (1,500 rpm, 4° C., 15 minutes) and suspended in 20 ml of a PBS again and then centrifuged again. The pellet thus obtained was combined with 11 ml of Solution 2 of DNA Extraction Kit (Stratagene, Catalog No.200600) and 4.8 µl of pronase, shaken at 60° C. for 2 hour, and then allowed to stand on ice for 10 minutes. Then the mixture was combined with 4 ml of Solution 3 of the kit described above and allowed to stand on ice for 5 minutes. The mixture was centrifuged (3,000 rpm, 4° C., 15 minutes) to recover a supernatant. The supernatant thus obtained was combined with an RNase at a ratio of 2 µl per 1 ml of the supernatant, and allowed to stand at 37° C. for 15 minutes. This mixture was combined with 2-volume ethanol and mixed to form a white string-like substance (genome DNA), which was then recovered. The genome DNA thus recovered was washed with 70% ethanol and then air-dried. The air-dried genome DNA was dissolved in 500 µl of 10 mM Tris-HCl/1 mM EDTA (pH 8.0) (hereinafter abbreviated as TE).

1 µg of the genome DNA thus dissolved and each 1 µl of an oligonucleotide consisting of the nucleotide sequence represented by SEQ ID No:17 and an oligonucleotide consisting of the nucleotide sequence represented by SEQ ID No:18 (10 pmol/µl), 29 µl of distilled water, 5 µl of a buffer included in TaKaRa LA Taq (TAKARA, Catalog No.RR002A), 5 µl of a $Mg^{2+}$ solution, 5 µl of dNTP mixture and 0.5 µl of TaKaRa LA Taq (TAKARA, Catalog No.RR002A) were mixed. The reaction mixture thus obtained was kept at 94° C. for 5 minutes, subjected to 30 cycles, each cycle involving the incubations at 94° C. for 1 minute, 60° C. for 1 minute and then 72° C. for 1 minute. This reaction solution subjected to a 2% agarose gel electrophoresis to recover an about 0.5 kb DNA. The DNA thus recovered was subjected to a phenol-chloroform treatment followed by an ethanol precipitation, whereby recovering a DNA. The DNA thus recovered was combined with an ultrapure water, and the solution was combined with 2.5 µl of NheI and 2.5 µl of HindIII, kept at 37° C. for 3 hours, and then the solution was subjected to a 2% agarose gel electrophoresis to recover an about 0.5 kb DNA. The DNA thus recovered was subjected to an ethanol precipitation to recover a DNA again (hereinafter designated as collagen promoter DNA). On the other hand, a vector having a nucleotide sequence encoding a firefly luciferase, namely pGL3 (Promega, Catalog No.E1751), was digested with NheI and HindIII, and subjected to an agarose gel electrophoresis as described above, whereby recovering an about 5 kb DNA (hereinafter designated as Luc vector DNA). The DNA thus recovered was subjected to an ethanol precipitation to recover a DNA again. The DNA thus recovered was combined with 44 µl of distilled water, 5 µl of Buffer attached to Alkaline Phosphatase (TAKARA, Catalog No.2120A) and 1 µl of Alkaline Phosphatase (TAKARA, Catalog No.2120A) and the mixture was kept at 65° C. for 30 minutes. Then the mixture was subjected twice to a phenol-chloroform treatment (hereinafter this procedure is referred to as BAP treatment 2). Subsequently, about 20 ng of the collagen promoter DNA and about 20 ng of Luc vector DNA described above were mixed, and the mixture was combined with an equal volume of an enzyme solution of DNA Ligation kit Ver 2, and then kept at 16° C. over one whole day and night. To this mixture, an $E.$ $coli$ 5Hdα (TOYOBO, Catalog No.DNA-903) was added and the mixture was allowed to stand on ice for 30 minutes and kept at 42° C. for 45 seconds, and the resultant $E.$ $coli$ was inoculated onto an LB plate containing 50 µg/ml sodium ampicillin (NACALAI, Catalog No.027-39), and allowed to stand at 37° C. over one whole day and night. A single colony which had emerged was incubated in 2 ml of an LB medium containing 50 µg/ml sodium ampicillin at 37° C. for 12 hours. From the resultant culture fluid, a plasmid DNA was prepared using AUTOMATIC DNA ISOLATION SYSTEM PI-50 (KURABO) to obtain a plasmid DNA. The nucleotide sequence of the plasmid DNA thus obtained was analyzed using a DNA sequencer, which revealed that a nucleotide sequence ligated to a firefly luciferase-encoding nucleotide sequence downstream of the nucleotide sequence from −342 to +57 (transcription starting point is +1) in the promoter region of a human type-I collagen α2 strand gene was possessed (hereinafter designated as COL-Luc).

(2) Preparation of Vector Expressing DNA-binding Protein of Invention

The total RNA solution prepared in Example 1 (1) and THERMOSCRIPT RTR-PCR System (Gibco BRL, Catalog No.11146-024) were employed to perform a reverse transcription reaction. Thus, 1 µg of the total RNA solution, 1 µl of Oligo(dT)$_{20}$ and DEPC-treated water were combined to obtain a total volume of 10 µl, and immediately after keeping at 65° C. for 5 minutes the mixture was cooled on ice. Then the mixture was combined with 4 µl of 5×cDNA synthesis Buffer, 1 µl of RNaseOUT, 1 µl of DTT, 1 µl of DEPC-treated water, 2 µl of 10 mM dNTP Mix and 1 µl of THERMOSCRIPT RT, and the mixture was kept at 55° C. for 1 hour followed by 85° C. for 5 minutes. Then the mixture was combined with 1 µl of RNase H, and kept at 37° C. for 20 minutes. 1 µl of the mixture thus obtained, 1 µl of an oligonucleotide consisting of the nucleotide sequence represented by SEQ ID No:.19 (10 pmol/µl), 1 µl of an oligonucleotide consisting of the nucleotide sequence represented by SEQ ID No:.20 (10 pmol/µl), 29 µl of distilled water, 5 µl of the buffer included in TaKaRa LA Taq (TAKARA, Catalog No.RR002A), 5 µl of a $Mg^{2+}$ solution, 5 µl of dNTP mixture and 0.5 µl of LA Taq were mixed and then the mixture thus obtained was kept at 94° C. for 5 minutes. Then the mixture was subjected to 35 cycles, each cycle involving the incubations at 94° C. for 1 minute, 60° C. for 1 minute and then 72° C. for 2 minutes, and further kept at 72° C. for 7 minutes. The mixture after these incubations was stored at 4° C. The mixture thus stored was subjected to an electrophoresis on 1% Agarose L gel. An about 1 kb DNA-containing gel portion was cut out, subjected to an ethanol precipitation to recover a DNA. The DNA thus recovered was combined with 40 µl of distilled water, 5 µl of 10×H Buffer, 2.5 µl of HindIII (Takara, Catalog No. 1060A) and 2.5 µl of XbaI (Takara, Catalog No. 1093A), and the mixture was kept at 37° C. for 3 hours. This mixture was then subjected to a 1% agarose gel electrophoresis to recover an about 1 kb DNA. The DNA thus recovered was subjected to an ethanol precipitation and the resultant pellet (DNA) was dissolved in 20 µl f a TE solution.

On the other hand, pRc/RSV (Invitrogen, Catalog No. 28-0051) was digested with HindIII and XbaII and the digestion product was subjected to a BAP treatment followed by an ethanol precipitation. The resultant pellet (DNA) was ligated with the about 1 kb DNA obtained above. The plasmid thus constructed was designated as YB-1/RSV.

(3) Preparation of Vector Expressing DNA-binding Protein as Partial Fragment

Using YB-1/RSV as a template together with an oligonucleotide consisting of the nucleotide sequence represented by SEQ ID No:23 and an oligonucleotide consisting of the nucleotide sequence represented by SEQ ID No:24 as primers, a PCR was performed similarly to Section (2) described above to prepare a DNA having a nucleotide sequence encoding the amino- acid sequence from the 1st to the 129th amino acids from the N-terminal of a human YB-1 (hereinafter designated as YB del DNA). The YB del DNA was digested with HindIII and XbaI, and ligated with a DNA of pRc/RSV digested with HindIII and XbaI. The resultant plasmid was designated as YB del/RSV.

(4) Quantification of Reporter Gene Expression

A normal human fetal dermal fibroblast was inoculated to a 60-mm dish at a population of $1 \times 10^6$ cells, and incubated in a Dulbecco's-MEM medium (NISSUI SEIYAKU, Catalog No.5919) (hereinafter referred to as D-MEM(+)) at 37° C. under 5% $CO_2$ atmosphere. Then the medium was replaced with a FBS-free Dulbecco's-MEM medium (hereinafter referred to as D-MEM(−)).

100 µl of D-MEM(−) was combined with 50 ng of YB-1/RSV or pRc/RSV and 4 µg of COL-Luc, and the mixture was allowed to stand at room temperature for 45 minutes (Solution 1). 100 µl of D-MEM(−) was combined also with 6 µl of Lipofectin (Gibco, Catalog No.18292-011), and the mixture was allowed to stand at room temperature for 40 minutes (Solution 2). Subsequently, Solution 1 and Solution 2 were mixed and allowed to stand at room temperature for 10 minutes, and then combined with 1.8 ml of D-MEM(−) and mixed. After adding this mixture to the normal human fetal dermal fibroblast described above, the cell was incubated at 37° C. under 5% $CO_2$ atmosphere for 6 hours. Thereafter, the dish was made free of the supernatant, and the cell was washed twice with D-MEM(−), combined with 4 ml of a Dulbecco's-MEM medium containing 0.1% FBS [hereinafter referred to as D-MEM(0.1%)] and incubated at 37° C. under 5% $CO_2$ atmosphere for 1 hour. This cell was combined with 4 µl of a 5 µg/ml aqueous solution of TGFβ (Pepro Tech, Catalog No) which is a positive regulatory factor of a collagen accumulation-promoting pathway (TGFβ concentration in medium: 5 ng/ml) and incubated at 37° C. under 5% $CO_2$ atmosphere further for 40 hours. In a case of TGFβ -free, 4 µl of distilled water was used instead of TGFβ. The cell thus incubated was washed twice with a PBS, combined with 150 µl of a cell lysis reagent (TOYO INK, Catalog No.PD10) and scraped from the wall of the vessel using a cell scraper (Nalgen, Catalog No.179693). The cell suspension thus obtained was recovered and then centrifuged (15,000 rpm, 4° C., 5 minutes) to recover a supernatant. Each 15 µl of the supernatant was transferred into a 96-well microplate, to which 50 µl of a Luc Assay solution (20 mM Tricine (pH7.8), 2.67 mM $MgSO_4$, 0.1 mM EDTA, 33.3 mM DTT, 270 µM Coenzyme A, 530 µM ATP, 470 µM Luciferin) was dispensed automatically using MICROLUMAT LB96P (EG&G BERTHOLD) and then the luminescence from each well was determined (Delay: 1.6 seconds, Meas. Interval: 5 seconds).

On the other hand, 5 µl of the recovered supernatant was combined with 200 µl of a 5-fold diluted Protein Assay solution (Bio-Rad, Catalog No. 500-0006) which had previously been dispensed into a 96-well plate, shaken, and then subjected to a determination of the absorbance at 595 nm in each well using a microplate reader (Bio-Rad, Benchmark). In a case of negative control, 5 μl of a cell lysis reagent was employed instead of the supernatant. Based on the value obtained in the determination described above, a promoter activity was calculated in accordance with the following equation. Promoter activity=[Luc activity (in a case of supernatant)−Luc activity (in a case of cell lysis reagent)]/[595 nm absorbance (in a case of supernatant)−595 nm absorbance (in a case of cell lysis reagent)] The results are shown in Table 6.

TABLE 6

| Expression vector | Presence or absence of DNA-binding protein of invention | Presence or absence of positive regulatory factor (TGFβ) of collagen accumulation promoting pathway | Relative promoter activity* | Remarks |
|---|---|---|---|---|
| pRc/RSV | Absence | Absence | 1.0 | |
| pRc/RSV | Absence | Presence | 3.4 | |
| YB-1/RSV | Absence | Absence | 1.7 | Vector expressing DNA-binding protein of invention |

*A relative promoter activity is a promoter activity in each case based on the promoter activity in a case of free of positive regulatory factor (TGFβ) of collagen accumulation promoting pathway in pRc/RSV-transduced cell as being regarded to be 1.0.

(2) Type-I Collagen Gene Transcription Regulating Ability of Test Substance Based on Reporter Gene Expression Level as Index As test substances, an angelica extract and a linden extract were employed.

2 ml of an angelica extract [ICHIMARU-PHARCOS, PHARCOLEX (trade mark of ICHIMARU-PHARCOS), angelica] and 2 ml of a basswood extract [ICHIMARU-PHARCOS, PHARCOLEX (trade mark of ICHIMARU-PHARCOS), linden] were freeze-dried and each was combined with 1 ml of dimethyl sulfoxide (hereinafter referred to as DMSO) per 50 mg of the freeze-dried material, whereby obtaining an angelica extract sample and a linden extract sample.

A normal human fetal dermal fibroblast was inoculated in a population of 1×10⁶ cells in a 60-mm dish and incubated in D-MEM (+) overnight at 37° C. under 5% $CO_2$ atmosphere, and then the culture medium was replaced with D-MEM (−). On the other hand, 100 μl of D-MEM (−) was combined with either of 2 μg of the binding reporter vector DNA or 2 μg of the non-binding reporter vector DNA obtained in Example 2 (3), and the mixture was allowed to stand at room temperature for 40 minutes (Solution 1). To 100 μl of MEM(−), 4.5 μl of Lipofectine (Gibco, Catalog No.18292-011) was added and the mixture was allowed to stand at room temperature for 40 minutes (Solution 2). Then Solution 1 and Solution 2 were mixed and allowed to stand at room temperature for 10 minutes, and then combined with 2 ml of D-MEM (−) and mixed. This mixture was added to the normal human fetal fibroblast described above, which was then incubated at 37° C. under 5% $CO_2$ atmosphere for 6 hours. Subsequently, the culture supernatant was removed from the dish and the cell was washed twice with D-MEM(−), combined with 4 ml of D-MEM(+), and then incubated at 37° C. under 5% $CO_2$ atmosphere further for 1 hour.

The angelica extract sample or the linden extract sample described above was diluted to 1 mg freeze-dried material/ml DMSO. Each 4 μl of the diluted solution thus obtained was added to the normal human fetal fibroblast described above (sample concentration in medium: 1 μg freeze dried material/ml, DMSO concentration in medium: 0.1%), and incubated at 37° C. under 5% $CO_2$ atmosphere for 40 hours. In a case of negative control, 4 μl of DMSO was employed instead of the sample (added at 0.1% DMSO in medium). In a case of positive control, interferon-γ (hereinafter referred to as IFN-γ. Roche, Catalog No.1040596) was added instead of the sample at 100 U/ml of INF-γ in the medium.

The cell thus incubated was washed twice with a PBS, and then examined for its CAT activity similarly to Example 2 (4).

The results are shown in Table 7. It was revealed that each sample reduced the expression level of the reporter gene. Thus, each of the angelica extract and the linden extract was proven to have a sufficient type-I collagen gene transcription regulating ability. Accordingly, it was proven that the method of the present invention can readily select a substance having a type-I collagen gene transcription regulating ability.

TABLE 7

| | Relative CAT activity* | |
|---|---|---|
| Test substance | Binding reporter vector-transduced cell | Non-binding reporter vector-transduced cell |
| Negative control | 1.0 | 0.9 |
| Linden extract sample | 0.7 | 0.9 |
| Angelica extract sample | 0.5 | 0.9 |
| Positive control | 0.6 | 0.9 |

*A relative CAT activity is a CAT activity in each case based on the CAT activity in a case of negative control of a cell into which the binding reporter vector has been transduced as being regarded to be 1.0.

Example 8

Collagen Accumulation Inhibitor: Substance having Type-I Collagen Gene Transcription Regulating Ability (1) Compound Extracted and Purified from Angelica
(1-1) Extraction and Purification of Compound from Angelica 3 kg of the fruit peel of an angelica was immersed in 25 kg of ethanol for 10 days, and then the mixture was filtered to recover a filtrate. The filtrate thus obtained was concentrated under reduced pressure and the concentrate thus obtained was made free of the supernatant, from which a 2 g aliquot was mixed with 3 ml of a 1:1 (v/v) mixture of ethanol and water. This mixture was applied onto a silica gel TLC plate (Merck, Art. 5744, 20×20 cm, 0.5 mm thickness) (20 plates in total) and developed with a 8:1 (v/v) mixture of chloroform and methanol. The fraction whose Rf vale was 0 to 0.05 was scraped and eluted with 50 ml of a 9:1 (v/v) mixture of methanol and water. The effluent was evaporated into dryness under a nitrogen flow, and the residue was dissolved in 1 ml of a 1:1 (v/v) mixture of methanol and water. This solution was applied onto a silica gel TLC plate (10 plates in total) and developed with a 30:10:1 (v/v/v) mixture of chloroform, methanol and water. The fraction whose Rf value was 0.7 was scraped and eluted with 30 ml of methanol. The effluent was evaporated under reduced pressure to remove the solvent, and the residue was dissolved in 1 ml of methanol. This solution was subjected to a high pressure liquid chromatography on a YMC-Pack ODS AM column (YMC, 10 mmID×25 cm) (eluent: 1:1 (v/v) mixture of methanol and water). The fraction whose retention time was 29 minutes was obtained and the effluent thus obtained was made free of the solvent by a distillation under reduced pressure to obtain Compound A (0.5 mg).

(1-2) Characterization of Extracted and Purified Compound

Compound A was examined for its characteristics.

$^1$H-NMR spectrum $^1$H-NMR (CD$_3$OD) δ: 1.14 (3 H, d, J=6.3 Hz), 1.17 (6 H, s), 2.29-2.40 (4 H, m), 3.25 (2 H, s), 3.65-3.68 (1 H, m), 3.95 (1 H, dd, J=5.5 Hz, 6.2 Hz), 5.44 (1 H, dt, J=5.4 Hz, 10.4 Hz), 5.76 (1 H, dd, J=6.5 Hz, 15.3 Hz), 6.00-6.07 (2 H, m), 6.58 (1 H, dd, J=10.9 Hz, 15.7 Hz), 6.79 (1 H, d, J=15.1 Hz)

Mass spectrum

FAB-MS: 298 [M+H]+, HRMS: 298.2019 [M+H]+

Molecular formula: C$_{16}$H$_{28}$NO$_4$

Structure

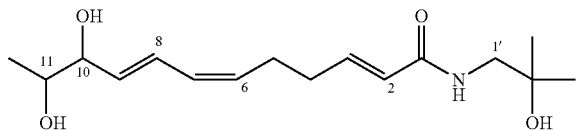 [SMILES: CC(O)C(O)/C=C/C=C\CC/C=C/C(=O)NCC(C)(C)O]

(1-3) Type-I Collagen Gene Transcription Regulating Ability of Compound A

Similarly to Example 8(2), a normal human fetal dermal fibroblast into which a binding reporter vector had been transduced was employed to examine Compound A for its type-I collagen gene transcription regulating ability. This cell was brought into contact with a methanol solution of Compound A (test substance) adjusted at a final concentration in the medium of 8 μM. In a case of negative control, an equal amount of methanol was employed instead of the methanol solution of Compound A. As a result, the group in which Compound A was brought into contact exhibited a relative CAT activity (CAT activity in a case of the tested compoud based on the CAT activity in the case of negative control as being regarded as 1.0) of 0.7, indicating that Compound A had a type-I collagen gene transcription regulating ability. Thus, Compound A was proven to be an active ingredient of a collagen accumulation inhibitor.

Example 9

Method for Inhibiting Collagen Accumulation by Administration of Positive Factor of Collagen Inhibiting Pathway which is Dependent on DNA-binding Protein of Invention: Determination of Collagen Accumulation Inhibiting Ability of Test Substance in Hepatic Fibrosis Model Mice (1) Sample Preparation Each of the freeze-dried material of an angelica extract [ICHIMARU-PHARCOS, PHARCOLEX (trade mark of ICHIMARU-PHARCOS), angelical and a basswood extract [ICHIMARU-PHARCOS, PHARCOLEX (trade mark of ICHIMARU-PHARCOS), linden] was combined with physiological saline (0.9% aqueous solution of sodium chloride) at a rate of 150 mg freeze-dried material/ml, mixed to obtain an angelica extract sample and a linden extract sample. As a positive factor for a collagen accumulation-promoting pathway, a carbon tetrachloride solution obtained by mixing a carbon tetrachloride (WAKO, Catalog No.030-15731) with an equal amount of a corn oil (NACALAITESQUE, Catalog No.256-06) until an uniform mixture was obtained was employed.

(2) Sample Administration

A 7-week old Balb/c mouse (Nippon Charles River, weighing 25 to 30 g) was treated with 0.5 g freeze-dried material/kg body weight (100 μl/30 g body weight) of the angelica extract sample or the linden extract sample obtained in Section (1) described above using an oral Sonde (FUCHIGAMI KIKI, Catalog No.6202) once a day for 4 weeks continuously. 3.5 ml/kg body weight of the carbon tetrachloride solution was given orally 4 times onece a week starting from one week after the initiation of the administration of the angelica extract sample or the linden extract sample (hereinafter referred to as in a case of angelica and in a case of linden). A group in which 100 μl/30 g body weight of physiological saline was given instead of the respective extract sample orally once a day for 4 weeks continuously and 3.5 ml/kg body of only the corn oil was given orally instead of the carbon tetrachloride solution (hereinafter referred to as in a case of non-treatment) and a group in which 100 μl/30 g body weight of physiological saline was given instead of the respective extract sample orally once a day for 4 weeks continuously and a carbon tetrachloride solution was given orally onece a week 4 times in total (hereinafter referred to as in a case of control) were also provided. Each group included 2 mice. 1 Week after the final administration of the angelica extract sample or the linden extract sample, each mouse was anesthetized with ether, and the hepatic medial lobe was isolated. Immediately after isolation, the hepatic medial lobe was immersed in a liquid nitrogen.

(3) Determination of Collagen Accumulation Inhibiting Ability

A boric acid buffer was prepared by dissolving 6.18 g of boric acid and 22.5 g of KCl in distilled water, adjusting at pH 8.7 with potassium hydroxide and making the total volume 100 ml. A chloramine T solution was prepared by dissolving 1.41 g of chloramine T (NACALAITESQUE, Catalog No.080-05) in 25 ml of 2-methoxyethanol (NACALAITESQUE, Catalog No.153-10). A p-dimethylaminobenzaldehyde solution was prepared by dissolving 12 g of p-dimethylaminobenzaldehyde (NACALAITESQUE, Catalog No.128-16) in 20 ml of ethanol followed by adding a mixture of 2.74 ml of concentrated sulfuric acid and 20 ml of ethanol slowly to the solution with cooling on ice. A hydroxyproline conventional solution was prepared by dissolving 3 mg of hydroxy-L-proline (NACALAITESQUE, Catalog No.188-17) in 1 ml of distilled water (3 mg/ml).

About 50 mg of the hepatic medial lobe prepared in Section (2) described above was weighed into a 13×100 mm screwed Pyrex tube (IWAKI, Catalog No.TST-SCR13-100), and hydrolyzed with 1 ml of 6 N HCl at 110° C. for 20 hours. The hydrolysate thus obtained was combined with 1 ml of 5 M potassium hydroxide, and the solution was filtered through a filter (0.22 μm, MILLIPORE, Catalog No.SLGP-R25LS), and the filtrate was collected. 1 ml of the filtrate thus recovered was combined with 1 ml of distilled water to use as a sample solution in the following procedure. 0, 1, 2 or 4 μl of the hydroxyproline conventional solution (corresponding to 0, 3, 6 or 12 μg of hydroxyproline, respectively) were combined with 2 ml of distilled water and used as conventional solutions. Each of the sample solutions and the conventional solutions was combined with 1.5 g of KCl, 0.25 ml of a 10% aqueous solution of alanine (pH 8.7) and 0.5 ml of a boric acid buffer, and the mixture was allowed to stand at room temperature for 30 minutes. The mixture was combined with 0.5 ml of the chloramine T solution, and allowed to stand for 25 minutes. This mixture was then combined with 1.5 ml of 3.6 M sodium thiosulfate (NACALAITESQUE, Catalog No.320-06) and 2.5 ml of toluene, and then capped and stirred for 5 minutes. After centrifuging the mixture at 1500 rpm for 5 minutes, the upper toluene layer was removed with suction and the remaining lower layer was collected. The solution thus obtained was kept at 100° C. for 30 minutes. The solution was cooled with a running water, combined with 2.5 ml of toluene again and then stirred for 5 minutes. The mixture was centrifuged at 1500 rpm for 5 minutes, and the toluene layer was collected. 1.25 ml of the toluene layer thus obtained was combined with 0.5 ml of the p-dimethylaminobenzaldehyde solution and allowed to stand at room temperature for 30 minutes, and then the mixture was examined for its absorbance at 560 nm. By producing a calibration curve from the values of the hydroxyproline conventional solutions (hydroxyproline 0 μg serving as a blank), the following equation was obtained.

Amount of hydroxyproline (μg)=17.416×[(absorbance of sample)−(absorbance of blank)]−0.1619, $R^2$=0.9954

Using this equation, the amount of hydroxyproline in a sample was determined, whereby calculating the amount of hydroxyproline present in 1 g of liver. The results are shown in Table 8.

As a result, a collagen accumulation inhibiting effect was observed in the angelica extract sample treatment group and also in the linden extract sample treatment group. Thus, each of the angelica extract and the linden extract was proven to be able to serve as an active ingredient of a collagen accumulation inhibitor.

TABLE 8

|  | Relative amount of hydroxyproline* |
|---|---|
| Non-treatment | 1.0 |
| Control | 1.5 |
| Angelica extract sample treatment | 1.1 |
| Linden extract sample treatment | 1.1 |

*A relative amount of hydroxyproline is a hydroxyproline amount in each case based on the hydroxyproline amount in a case of non-treatment as being regarded as 1.0.

SEQUENCE FREE TEXT

SEQ ID No:2
An oligonucleotide designed for the preparation of a DNA consisting of the nucleotide sequence to which the protein of the present invention are bound
SEQ ID No:3
An oligonucleotide designed for the preparation of a DNA consisting of the nucleotide sequence to which the protein of the present invention are bound
SEQ ID No:4
An oligonucleotide designed for the preparation of a DNA consisting of the nucleotide sequence to which the protein of the present invention are not bound
SEQ ID No:5
An oligonucleotide primer designed for PCR amplification
SEQ ID No:6
An oligonucleotide primer designed for PCR amplification
SEQ ID No:7
An oligonucleotide designed for the preparation of a DNA consisting of the nucleotide sequence to which the protein of the present invention are not bound
SEQ ID No:8
An oligonucleotide primer designed for PCR amplification
SEQ ID No:9
An oligonucleotide primer designed for PCR amplification
SEQ ID No:10
An oligonucleotide primer designed for PCR amplification
SEQ ID No:11
An oligonucleotide primer designed for PCR amplification
SEQ ID No:12
An oligonucleotide primer designed for PCR amplification
SEQ ID No:13
An oligonucleotide primer designed for PCR amplification
SEQ ID No:14
An oligonucleotide primer designed for POR amplification
SEQ ID No:15
An oligonucleotide primer designed for PCR amplification
SEQ ID No:16
An oligonucleotide primer designed for PCR amplification
SEQ ID No:17
An oligonucleotide primer designed for the amplification of collagen promoter DNA
SEQ ID No:18
An oligonucleotide primer designed for the amplification of collagen promoter DNA
SEQ ID No:19
An oligonucleotide primer designed for the preparation of expression vector expressing the protein of the present invention
SEQ ID No:20
An oligonucleotide primer designed for the preparation of expression vector expressing the protein of the present invention
SEQ ID No:21
An oligonucleotide primer designed for the preparation of alpha 1 DNA probe of I-type collagen gene
SEQ ID No:22
An oligonucleotide primer designed for the preparation of alpha 1 DNA probe of I-type collagen gene
SEQ ID No:23
An oligonucleotide primer designed for PCR amplification
SEQ ID No:24
An oligonucleotide primer designed for PCR amplification
SEQ ID No:25
An oligonucleotide designed for the preparation of a DNA consisting of the nucleotide sequence to which the protein of the present invention are not bound.

What is claimed is:

1. A method for inhibiting collagen accumulation in a mammal in need of such treatment, said method comprising administering to a mammalian cell(s) of said mammal an exogenous gene encoding a DNA-binding protein said DNA-binding protein having any of the following amino acid sequences so that said exogenous gene is located in a position enabling its expression in said mammalian cell(s):
   (a) the amino acid sequence represented by SEQ ID NO:1, which is an amino acid sequence of a protein having an ability of inhibiting the transcription of a type-I collagen gene;
   (b) an amino acid sequence whose sequence identity with the amino acid sequence represented by SEQ ID NO:1 is 80% or more and which is an amino acid sequence of a protein having an ability of inhibiting the transcription of a type-I collagen gene;
   (c) an amino acid sequence encoded by a DNA having a nucleotide sequence whose sequence identity with a DNA having a nucleotide sequence encoding the amino acid sequence represented by SEQ ID NO:1 is 90% or more and which is an amino acid sequence of a protein having an ability of inhibiting the transcription of a type-I collagen gene; and
   (d) an amino acid sequence encoded by a DNA capable of being hybridized under a stringent condition with a DNA having a nucleotide sequence encoding the amino acid sequence represented by SEQ ID NO:1 and which is an amino acid sequence of a protein having an ability of inhibiting the transcription of a type-I collagen gene, wherein the stringent condition comprises hybridization at 45° C. in the presence of a 6×SSC solution, and washing at 65° C. with a 0.2×SSC solution,
   and wherein for (b) or (c), the sequence identity is about 100% for the 52nd to 130th amino acids and at least 50% for the 1st to 51st amino acids.

2. The method for inhibiting collagen accumulation according to claim 1 wherein said exogenous gene is provided to a mammalian cell outside of which a positive regulatory factor of a collagen accumulation-promoting pathway is present.

3. The method for inhibiting collagen accumulation according to claim 2 wherein the positive regulatory factor of a collagen accumulation-promoting pathway is a positive regulatory factor of a DNA-binding protein-dependent collagen accumulation promoting pathway.

4. The method for inhibiting collagen accumulation according to claim 3, wherein the DNA-binding protein-dependent collagen accumulation promoting pathway is an AP-1-dependent collagen accumulation promoting pathway or a Smad-dependent collagen accumulation promoting pathway.

5. The method for inhibiting collagen accumulation according to claim 2 wherein the positive regulatory factor of a collagen accumulation-promoting pathway is a TGF-β.

6. The method for inhibiting collagen accumulation according to claim 2, wherein the amino acid sequence is represented by SEQ ID NO:1.

7. The method for inhibiting collagen accumulation according to claim 1, wherein the amino acid sequence has 80% or more sequence identity with amino acid sequence represented by SEQ ID NO:1 and which is an amino acid sequence of a protein having an ability of inhibiting the transcription of type-I collagen gene.

8. The method for inhibiting collagen accumulation according to claim 1, wherein the amino acid sequence has 90% or more sequence identity with amino acid sequence represented by SEQ ID NO:1 and which is an amino acid sequence of a protein having an ability of inhibiting the transcription of type-I collagen gene.

9. The method for inhibiting collagen accumulation according to claim 1, wherein the amino acid sequence is (d).

10. A method for inhibiting collagen accumulation according to claim 1, wherein the DNA-binding protein has a molecular weight of about 40 kDA to about 60 kDa, as determined by SDS-Page.

11. A method for inhibiting collagen accumulation according to claim 1, wherein said DNA-binding protein is (b) or (c) and said sequence identity is about 100% for amino acids 1-129 of SEQ ID NO:1.

12. A method for inhibiting collagen accumulation according to claim 1, wherein the amino acid sequence is represented by SEQ ID NO:1.

13. A method for providing an exogenous gene encoding a DNA-binding protein to mammalian cells to inhibit collagen accumulation in said cells, said method comprising introducing an exogenous gene in mammalian cells, said exogenous gene encoding a DNA-binding protein having at least one of the following sequences:
  (a) the amino acid sequence represented by SEQ ID NO:1, which is an amino acid sequence of a protein having an ability of inhibiting the transcription of a type-I collagen gene;
  (b) an amino acid sequence whose sequence identity with the amino acid sequence represented by SEQ ID NO:1 is 80% or more and which is an amino acid sequence of a protein having an ability of inhibiting the transcription of a type-I collagen gene;
  (c) an amino acid sequence encoded by a DNA having a nucleotide sequence whose sequence identity with a DNA having a nucleotide sequence encoding the amino acid sequence represented by SEQ ID NO:1 is 90% or more and which is an amino acid sequence of a protein having an ability of inhibiting the transcription of a type-I collagen gene; and
  (d) an amino acid sequence encoded by a DNA capable of being hybridized under a stringent condition with a DNA having a nucleotide sequence encoding the amino acid sequence represented by SEQ ID NO:1 and which is an amino acid sequence of a protein having an ability of inhibiting the transcription of a type-I collagen gene, wherein the stringent condition comprises hybridization at 45° C. in the presence of a 6×SSC solution, and washing at 65° C. with a 0.2×SSC solution,
  and wherein for (b) or (c), the sequence identity is about 100% for the 52nd to 130th amino acids and at least 50% for the 1st to 51st amino acids,
  and said exogenous gene is located in a position enabling its expression in said mammalian cells.

14. The method for providing an exogenous gene encoding a DNA-binding protein to mammalian cells according to claim 13, wherein the protein has an ability to inhibit the transcription of type-I collagen gene, and said protein has the amino acid sequence of SEQ ID NO:1.

* * * * *

SEQUENCE LISTING

<160> NUMBER OF SEQ ID NOS: 26

<210> SEQ ID NO 1
<211> LENGTH: 317
<212> TYPE: PRT

-continued

<213> ORGANISM: HOMO SAPIENS

<400> SEQUENCE: 1

Met Ser Ser Glu Ala Glu Thr Gln Gln Pro Pro Ala Ala Pro Pro Ala
1               5                   10                  15

Ala Pro Ala Leu Ser Ala Ala Asp Thr Lys Pro Gly Thr Thr Gly Ser
            20                  25                  30

Gly Ala Gly Ser Gly Gly Pro Gly Gly Leu Thr Ser Ala Ala Pro Ala
        35                  40                  45

Gly Gly Asp Lys Lys Val Ile Ala Thr Lys Val Leu Gly Thr Val Lys
    50                  55                  60

Trp Phe Asn Val Arg Asn Gly Tyr Gly Phe Ile Asn Arg Asn Asp Thr
65                  70                  75                  80

Lys Glu Asp Val Phe Val His Gln Thr Ala Ile Lys Lys Asn Asn Pro
                85                  90                  95

Arg Lys Tyr Leu Arg Ser Val Gly Asp Gly Glu Thr Val Glu Phe Asp
            100                 105                 110

Val Val Glu Gly Glu Lys Gly Glu Glu Ala Ala Asn Val Thr Gly Pro
        115                 120                 125

Gly Gly Val Pro Val Gln Gly Ser Lys Tyr Ala Ala Asp Arg Asn His
    130                 135                 140

Tyr Arg Arg Tyr Pro Arg Arg Arg Gly Pro Pro Arg Asn Tyr Gln Gln
145                 150                 155                 160

Asn Tyr Gln Asn Ser Glu Ser Gly Glu Lys Asn Glu Gly Ser Glu Ser
                165                 170                 175

Ala Pro Glu Gly Gln Ala Gln Gln Arg Arg Pro Tyr Arg Arg Arg Arg
            180                 185                 190

Phe Pro Pro Tyr Tyr Met Arg Arg Pro Tyr Gly Arg Arg Pro Gln Tyr
        195                 200                 205

Ser Asn Pro Pro Val Gln Gly Glu Val Met Glu Gly Ala Asp Asn Gln
    210                 215                 220

Gly Ala Gly Glu Gln Gly Arg Pro Val Arg Gln Asn Met Tyr Arg Gly
225                 230                 235                 240

Tyr Arg Pro Arg Phe Arg Arg Gly Pro Pro Arg Gln Arg Gln Pro Arg
                245                 250                 255

Glu Asp Gly Asn Glu Glu Asp Lys Glu Asn Gln Gly Asp Glu Thr Gln
            260                 265                 270

Gly Gln Gln Pro Pro Gln Arg Arg Tyr Arg Arg Asn Phe Asn Tyr Arg
        275                 280                 285

Arg Arg Arg Pro Glu Asn Pro Lys Pro Gln Asp Gly Lys Glu Thr Lys
    290                 295                 300

Ala Ala Asp Pro Pro Ala Glu Asn Ser Arg Ser Arg Gly
305                 310                 315

<210> SEQ ID NO 2
<211> LENGTH: 12
<212> TYPE: DNA
<213> ORGANISM: Artificial Sequence
<220> FEATURE:
<223> OTHER INFORMATION: DESIGNED OLIGONUCLEOTIDE TO SYNTHESIZE YB-1
      BINDING SEQUNCE

<400> SEQUENCE: 2
cccawtcgct cc                                                        12

<210> SEQ ID NO 3
<211> LENGTH: 38

```
<212> TYPE: DNA
<213> ORGANISM: Artificial Sequence
<220> FEATURE:
<223> OTHER INFORMATION: DESIGNED OLIGONUCLEOTIDE TO SYNTHESIZE YB-1
      BINDING SEQUENCE

<400> SEQUENCE: 3 cccccattc gctccctcct ctgcgccccc gcaggctc                          38

<210> SEQ ID NO 4
<211> LENGTH: 12
<212> TYPE: DNA
<213> ORGANISM: Artificial Sequence
<220> FEATURE:
<223> OTHER INFORMATION: DESIGNED OLIGONUCLEOTIDE TO SYNTHESIZE YB-1
      NON-BINDING SEQUENCE

<400> SEQUENCE: 4
cggawtcgct cc                                                     12

<210> SEQ ID NO 5
<211> LENGTH: 45
<212> TYPE: DNA
<213> ORGANISM: Artificial Sequence
<220> FEATURE:
<223> OTHER INFORMATION: DESIGNED OLIGONUCLEOTIDE PRIMER FOR PCR

<400> SEQUENCE: 5
ccaaggatcc cagtcaccat caccgcaacc atgagcagcg aggcc                 45

<210> SEQ ID NO 6
<211> LENGTH: 46
<212> TYPE: DNA
<213> ORGANISM: Artificial Sequence
<220> FEATURE:
<223> OTHER INFORMATION: DESIGNED OLIGONUCLEOTIDE PRIMER FOR PCR

<400> SEQUENCE: 6
ccaactcgag atttactcag ccccgccctg ctcagcctcg ggagcg                46

<210> SEQ ID NO 7
<211> LENGTH: 38
<212> TYPE: DNA
<213> ORGANISM: Artificial Sequence
<220> FEATURE:
<223> OTHER INFORMATION: DESIGNED OLIGONUCLEOTIDE TO SYNTHESIZE YB-1
      NON-BINDING SEQUENCE

<400> SEQUENCE: 7
ccccggattc gctccctcct ctgcgccccc gcaggctc                         38

<210> SEQ ID NO 8
<211> LENGTH: 34
<212> TYPE: DNA
<213> ORGANISM: Artificial Sequence
<220> FEATURE:
<223> OTHER INFORMATION: DESIGNED OLIGONUCLEOTIDE PRIMER FOR PCR

<400> SEQUENCE: 8
ccaaggatcc ctggtaaatc cagacaagga gccc                             34

<210> SEQ ID NO 9
<211> LENGTH: 34
<212> TYPE: DNA
<213> ORGANISM: Artificial Sequence
<220> FEATURE:
<223> OTHER INFORMATION: DESIGNED OLIGONUCLEOTIDE PRIMER FOR PCR
```

<400> SEQUENCE: 9
ccaaaagctt catgcagtcg tggccagtac ctcc                                34

<210> SEQ ID NO 10
<211> LENGTH: 28
<212> TYPE: DNA
<213> ORGANISM: Artificial Sequence
<220> FEATURE:
<223> OTHER INFORMATION: DESIGNED OLIGONUCLEOTIDE PRIMER FOR PCR

<400> SEQUENCE: 10
ccaaggatcc cccattcgct ccctcctc                                       28

<210> SEQ ID NO 11
<211> LENGTH: 28
<212> TYPE: DNA
<213> ORGANISM: Artificial Sequence
<220> FEATURE:
<223> OTHER INFORMATION: DESIGNED OLIGONUCLEOTIDE PRIMER FOR PCR

<400> SEQUENCE: 11
ccaaaagctt gcatgcagtc gtggccag                                       28

<210> SEQ ID NO 12
<211> LENGTH: 28
<212> TYPE: DNA
<213> ORGANISM: Artificial Sequence
<220> FEATURE:
<223> OTHER INFORMATION: DESIGNED OLIGONUCLEOTIDE PRIMER FOR PCR

<400> SEQUENCE: 12
ccaaggatcc cggattcgct ccctcctc                                       28

<210> SEQ ID NO 13
<211> LENGTH: 25
<212> TYPE: DNA
<213> ORGANISM: Artificial Sequence
<220> FEATURE:
<223> OTHER INFORMATION: DESIGNED OLIGONUCLEOTIDE PRIMER FOR PCR

<400> SEQUENCE: 13
ccacaaagaa ttcatggtca gcacc                                          25

<210> SEQ ID NO 14
<211> LENGTH: 24
<212> TYPE: DNA
<213> ORGANISM: Artificial Sequence
<220> FEATURE:
<223> OTHER INFORMATION: DESIGNED OLIGONUCLEOTIDE PRIMER FOR PCR

<400> SEQUENCE: 14
ctcgtggtgc tcatggtgct gtag                                           24

<210> SEQ ID NO 15
<211> LENGTH: 30
<212> TYPE: DNA
<213> ORGANISM: Artificial Sequence
<220> FEATURE:
<223> OTHER INFORMATION: DESIGNED OLIGONUCLEOTIDE PRIMER FOR PCR

<400> SEQUENCE: 15
ccaaaagctt atgagcagcg aggccgagac                                     30

<210> SEQ ID NO 16
<211> LENGTH: 24
<212> TYPE: DNA

```
<213> ORGANISM: Artificial Sequence
<220> FEATURE:
<223> OTHER INFORMATION: DESIGNED OLIGONUCLEOTIDE PRIMER FOR PCR

<400> SEQUENCE: 16
gcctcgggag cgggaattct cagc                                          24

<210> SEQ ID NO 17
<211> LENGTH: 32
<212> TYPE: DNA
<213> ORGANISM: Artificial Sequence
<220> FEATURE:
<223> OTHER INFORMATION: DESIGNED OLIGONUCLEOTIDE PRIMER TO AMPLIFY
      COLLAGEN PROMOTER DNA

<400> SEQUENCE: 17
ccaagctagc cgacgtgtcc catagtgttt cc                                 32

<210> SEQ ID NO 18
<211> LENGTH: 28
<212> TYPE: DNA
<213> ORGANISM: Artificial Sequence
<220> FEATURE:
<223> OTHER INFORMATION: DESIGNED OLIGONUCLEOTIDE PRIMER TO AMPLIFY
      COLLAGEN PROMOTER DNA

<400> SEQUENCE: 18
ccaaaagctt gcagtcgtgg ccagtacc                                      28

<210> SEQ ID NO 19
<211> LENGTH: 45
<212> TYPE: DNA
<213> ORGANISM: Artificial Sequence
<220> FEATURE:
<223> OTHER INFORMATION: DESIGNED OLIGONUCLEOTIDE PRIMER TO SYNTHESIZE
      YB-1 EXPRESSION VECTOR

<400> SEQUENCE: 19
ccaaaagctt cagtcaccat caccgcaacc atgagcagcg aggcc                   45

<210> SEQ ID NO 20
<211> LENGTH: 46
<212> TYPE: DNA
<213> ORGANISM: Artificial Sequence
<220> FEATURE:
<223> OTHER INFORMATION: DESIGNED OLIGONUCLEOTIDE PRIMER TO SYNTHESIZE
      YB-1 EXPRESSION VECTOR

<400> SEQUENCE: 20
ccaatctaga tttactcagc cccgccctgc tcagcctcgg gaggcg                  46

<210> SEQ ID NO 21
<211> LENGTH: 21
<212> TYPE: DNA
<213> ORGANISM: Artificial Sequence
<220> FEATURE:
<223> OTHER INFORMATION: DESIGNED OLIGONUCLEOTIDE PRIMER TO SYNTHESIZE
      COLLAGEN ALPHA 1 PROBE

<400> SEQUENCE: 21
aagggtgaaa gtggtcccag c                                             21

<210> SEQ ID NO 22
<211> LENGTH: 22
<212> TYPE: DNA
<213> ORGANISM: Artificial Sequence
<220> FEATURE:
<223> OTHER INFORMATION: DESIGNED OLIGONUCLEOTIDE PRIMER TO SYNTHESIZE
```

-continued

COLLAGEN ALPHA 1 PROBE

<400> SEQUENCE: 22
gcggcttccc tctgggctcc gg                                         22

<210> SEQ ID NO 23
<211> LENGTH: 30
<212> TYPE: DNA
<213> ORGANISM: Artificial Sequence
<220> FEATURE:
<223> OTHER INFORMATION: DESIGNED OLIGONUCLEOTIDE PRIMER FOR PCR

<400> SEQUENCE: 23
ccaaaagctt atgagcagcg aggccgagac                                 30

<210> SEQ ID NO 24
<211> LENGTH: 37
<212> TYPE: DNA
<213> ORGANISM: Artificial Sequence
<220> FEATURE:
<223> OTHER INFORMATION: DESIGNED OLIGONUCLEOTIDE PRIMER FOR PCR

<400> SEQUENCE: 24
ccaatctaga tcaaccagga cctgtaacat ttgctgc                         37

<210> SEQ ID NO 25
<211> LENGTH: 12
<212> TYPE: DNA
<213> ORGANISM: Artificial Sequence
<220> FEATURE:
<223> OTHER INFORMATION: DESIGNED OLIGONUCLEOTIDE TO SYNTHESIZE YB-1
       NON-BINDING SEQUENCE

<400> SEQUENCE: 25
crrawtcgct cc                                                    12

<210> SEQ ID NO 26
<211> LENGTH: 954
<212> TYPE: DNA
<213> ORGANISM: HOMO SAPIENS
<220> FEATURE:
<221> NAME/KEY: CDS
<222> LOCATION: (1)...(954)

<400> SEQUENCE: 26

| | | |
|---|---|---|
| atg agc agc gag gcc gag acc cag cag ccg ccc gcc gcc ccc ccc gcc<br>Met Ser Ser Glu Ala Glu Thr Gln Gln Pro Pro Ala Ala Pro Pro Ala<br>1               5                   10                  15 | | 48 |
| gcc ccc gcc ctc agc gcc gcc gac acc aag ccc ggc act acg ggc agc<br>Ala Pro Ala Leu Ser Ala Ala Asp Thr Lys Pro Gly Thr Thr Gly Ser<br>            20                  25                  30 | | 96 |
| ggc gca ggg agc ggt ggc ccg ggc ggc ctc aca tcg gcg gcg cct gcc<br>Gly Ala Gly Ser Gly Gly Pro Gly Gly Leu Thr Ser Ala Ala Pro Ala<br>        35                  40                  45 | | 144 |
| ggc ggg gac aag aag gtc atc gca acg aag gtt ttg gga aca gta aaa<br>Gly Gly Asp Lys Lys Val Ile Ala Thr Lys Val Leu Gly Thr Val Lys<br>    50                  55                  60 | | 192 |
| tgg ttc aat gta agg aac gga tat ggt ttc atc aac agg aat gac acc<br>Trp Phe Asn Val Arg Asn Gly Tyr Gly Phe Ile Asn Arg Asn Asp Thr<br>65                  70                  75                  80 | | 240 |
| aag gaa gat gta ttt gta cac cag act gcc ata aag aag aat aac ccc<br>Lys Glu Asp Val Phe Val His Gln Thr Ala Ile Lys Lys Asn Asn Pro<br>                85                  90                  95 | | 288 |
| agg aag tac ctt cgc agt gta gga gat gga gag act gtg gag ttt gat<br>Arg Lys Tyr Leu Arg Ser Val Gly Asp Gly Glu Thr Val Glu Phe Asp | | 336 |

-continued

```
                        100                     105                     110
gtt gtt gaa gga gaa aag ggt gag gag gca gca aat gtt aca ggt cct         384
Val Val Glu Gly Glu Lys Gly Glu Glu Ala Ala Asn Val Thr Gly Pro
            115                     120                     125
ggt ggt gtt cca gtt caa ggc agt aaa tat gca gca gac cgt aac cat         432
Gly Gly Val Pro Val Gln Gly Ser Lys Tyr Ala Ala Asp Arg Asn His
            130                     135                     140
tat aga cgc tat cca cgt cgt agg ggt cct cca cgc aat tac cag caa         480
Tyr Arg Arg Tyr Pro Arg Arg Arg Gly Pro Pro Arg Asn Tyr Gln Gln
145                     150                     155                     160
aat tac cag aat agt gag agt ggg gaa aag aac gag gga tcg gag agt         528
Asn Tyr Gln Asn Ser Glu Ser Gly Glu Lys Asn Glu Gly Ser Glu Ser
            165                     170                     175
gct ccc gaa ggc cag gcc caa caa cgc cgg ccc tac cgc agg cga agg         576
Ala Pro Glu Gly Gln Ala Gln Gln Arg Arg Pro Tyr Arg Arg Arg Arg
            180                     185                     190
ttc cca cct tac tac atg cgg aga ccc tat ggg cgt cga cca cag tat         624
Phe Pro Pro Tyr Tyr Met Arg Arg Pro Tyr Gly Arg Arg Pro Gln Tyr
            195                     200                     205
tcc aac cct cct gtg cag gga gaa gtg atg gag ggt gct gac aac cag         672
Ser Asn Pro Pro Val Gln Gly Glu Val Met Glu Gly Ala Asp Asn Gln
            210                     215                     220
ggt gca gga gaa caa ggt aga cca gtg agg cag aat atg tat cgg gga         720
Gly Ala Gly Glu Gln Gly Arg Pro Val Arg Gln Asn Met Tyr Arg Gly
225                     230                     235                     240
tat aga cca cga ttc cgc agg ggc cct cct cgc caa aga cag cct aga         768
Tyr Arg Pro Arg Phe Arg Arg Gly Pro Pro Arg Gln Arg Gln Pro Arg
            245                     250                     255
gag gac ggc aat gaa gaa gat aaa gaa aat caa gga gat gag acc caa         816
Glu Asp Gly Asn Glu Glu Asp Lys Glu Asn Gln Gly Asp Glu Thr Gln
            260                     265                     270
ggt cag cag cca cct caa cgt cgg tac cgc cgc aac ttc aat tac cga         864
Gly Gln Gln Pro Pro Gln Arg Arg Tyr Arg Arg Asn Phe Asn Tyr Arg
            275                     280                     285
cgc aga cgc cca gaa aac cct aaa cca caa gat ggc aaa gag aca aaa         912
Arg Arg Arg Pro Glu Asn Pro Lys Pro Gln Asp Gly Lys Glu Thr Lys
290                     295                     300
gca gcc gat cca cca gct gag aat tcc cgc tcc cga ggc tga             954
Ala Ala Asp Pro Pro Ala Glu Asn Ser Arg Ser Arg Gly  *
305                     310                     315
```